US007504426B2

(12) United States Patent
Carruthers et al.

(10) Patent No.: US 7,504,426 B2
(45) Date of Patent: Mar. 17, 2009

(54) HETEROCYCLIC COMPOUNDS

(75) Inventors: Nicholas I. Carruthers, Poway, CA (US); Curt A. Dvorak, San Diego, CA (US); James P. Edwards, San Diego, CA (US); Cheryl A. Grice, Carlsbad, CA (US); Jill A. Jablonowski, San Diego, CA (US); Kiev S. Ly, San Diego, CA (US); Barbara A. Pio, Hillsborough, NJ (US); Chandravadan R. Shah, San Diego, CA (US); Jennifer D. Venable, Del Mar, CA (US)

(73) Assignee: Janssen Pharmaceutica N.V., Beerse (BE)

( * ) Notice: Subject to any disclaimer, the term of this patent is extended or adjusted under 35 U.S.C. 154(b) by 690 days.

(21) Appl. No.: 10/655,381

(22) Filed: Sep. 4, 2003

(65) Prior Publication Data
US 2004/0058934 A1   Mar. 25, 2004

(51) Int. Cl.
C07D 235/00 (2006.01)
A01N 43/05 (2006.01)
A61K 31/415 (2006.01)

(52) U.S. Cl. .................. 514/396; 548/302.7; 548/304.4
(58) Field of Classification Search .............. 548/304.4, 548/302.4; 514/396
See application file for complete search history.

(56) References Cited

U.S. PATENT DOCUMENTS

| 4,115,569 A | 9/1978 | Weber et al. |
| 4,374,990 A | 2/1983 | Weber et al. |
| 4,820,757 A | 4/1989 | Stang et al. |
| 5,563,142 A | 10/1996 | Palmer et al. |
| 5,814,644 A | 9/1998 | Kulagowski et al. |
| 5,891,902 A | 4/1999 | Machii et al. |

FOREIGN PATENT DOCUMENTS

| DE | 2157424 A | 5/1973 |
| DE | 4307883 A1 | 9/1993 |
| EP | 0 127 066 A | 12/1984 |
| EP | 0318235 A2 | 5/1989 |
| EP | 0324431 A1 | 7/1989 |
| EP | 0 370 381 A | 5/1990 |
| EP | 0548798 A1 | 6/1993 |
| EP | 0624575 A1 | 11/1994 |
| EP | 0655440 A2 | 5/1995 |
| EP | 0978512 A1 | 2/2000 |
| JP | 59 036670 A | 2/1984 |
| JP | 01132579 A2 | 5/1989 |
| JP | 5025131 A | 2/1993 |
| JP | 09 124609 A | 5/1997 |
| JP | 9124631 A | 5/1997 |
| JP | 2003 104975 A | 4/2003 |
| SU | 1074094 A1 | 4/1992 |
| WO | WO 91/09849 A1 | 7/1991 |
| WO | WO 92/10491 A | 6/1992 |
| WO | WO 94/09781 | 5/1994 |
| WO | WO 97/03965 | 2/1997 |
| WO | WO 97/43271 A | 11/1997 |
| WO | WO 98/01443 | 1/1998 |
| WO | WO 99/09025 A2 | 2/1999 |
| WO | WO 99/58121 | 2/1999 |
| WO | WO 01/64676 A2 | 9/2001 |
| WO | WO 01/74774 A1 | 10/2001 |

OTHER PUBLICATIONS

Garuti, L. et al. Synthesis and antiviral assays of some 2-substituted benzimidazole-N-carbamates. Il Farmaco 55 (2000) 35-39.
Orjales, Aurelio et al., "Benzimidazole-2-carboxylic acid amides and esters: a new structural class fo 5-HT3 ligands", European Journal fo Medical Chemistry, vol. 34, No. 5, pp. 415-422 (1999).
Perrone, R. et al., "1-Substituted-4-'3-(1, 2, 3, 4-tetrahydro-5-or 7-methoxynaphthalen-1-yl)propyllpiperazines: influence of the N-1 piperazine substituent of 5-HT1A receptor affinity and selectivity versus D2 and.alpha.1 receptors. Part 6", Bioorganic & Medicinal Chemistry, vol. 8, No. 5, pp. 873-881 (2000).
Du, Jianhong et al., "Synthesis and bioactivity of benzimidazole-2-acyl compounds", Zhongguo Yaoke Daxue Xuebao, vol. 29, No. 4, pp. 243-246 (1998).
Rastogi, Rashmi et al., "Synthesis of benzimidazole-2-carboxamides as potential anthelmintic agents", Indian Journal of Chemistry, Section B: Organic Chemistry Including Medicinal Chemistry, vol. 18B, No. 5, pp. 464-467 (1979).
Al-Shaar, Adnan H.M. et al., "The reactions of C-methylheterocycles with thionyl chloride. Part 3, The transformation fo some five- and six-membered heterocycles", Journal of Heterocyclic Chemistry, vol. 26, No. 6, pp. 1819-1825 (1989).
PCT International Search Report, dated Feb. 23, 2004, for PCT Int'l. Appln. No. PCT/US03/27461.
Agarwal, A. et al. A New Synthesis of the Potent 5-HT1 Receptor Ligand, 5-Carboxyamidotryptamine (5-CT). Synth. Commun. (1993) 23(8):1101-1110.
Alvarez, E.F. et al. Psychotropes Potentiels. III. Préparation des [(Hydroxy-5 ou Benzyloxy-5 indolyl)-2 carbonyl]-1 alkyl-2 hydrazines et Etude de Leur Activité Inhibitrice de la Monoamine Oxydase. Bull. Soc. Chim. Fr. (1969) (6):1932-1940.
Ambekar, S.Y. Recent Developments in the Fischer Indole Synthesis. Current Science (1983) 52(12):578-582.
Betrabet, A.M. et al. Synthesis & Pharmacology of 5-Methoxyindole-2-carboxyamides & Their 3-Formyl Derivatives. Indian J. Chem. (1970) 8:704-706.
Bhandari, K. et al. Agents Acting on CNS: Part XXXIII—Synthesis of 1,2,3,4,6,7,8,12c-Octahydropyrazino[2',1'   :2,1]pyrido[4,3-b]indole & Some 2-Substituted Aminoalkylindoles. Indian J. Chem. (1979) 17B:246-249.
De Costa, B.R. et al. Synthesis and Evaluation of Conformationally Restricted N-[2-(3,4-Dichlorophenyl)ethyl]-N-methyl-2-(1-pyrrolidinyl)ethylamines at sigma Receptors. 2. Piperazines, Bicyclic Amines, Bridged Bicyclic Amines, and Miscellaneous Compounds. J. Med. Chem. (1993) 36:2311-2320.

(Continued)

Primary Examiner—James O. Wilson
Assistant Examiner—Paul V. Ward
(74) Attorney, Agent, or Firm—John Harbour

(57) ABSTRACT

Certain thienopyrrolyl and furanopyrrolyl compounds are disclosed as useful to treat or prevent disorders and conditions mediated by the histamine $H_4$ receptor, including allergic rhinitis.

19 Claims, No Drawings

OTHER PUBLICATIONS

Dubey, R. et al. Mass Spectral Studies of 2,5-Disubstituted Benzimidazoles. Indian J. Chem. (1987) 26B:395-397.

El-Kholy, I.E.-S. et al. Reaction of Some Coumarin and 4.6-Diaryl-2H-pyran Derivatives with Secondary Amines. J. Heterocyclic Chem. (1981) 18:105-110.

Font, M. et al. Indoles and Pyridazino[4,5-b]indoles as Non-Nucleoside Analog Inhibitors of HIV-1 Reverse Transcriptase. Eur. J. Med. Chem. (1995) 30:963-971.

Garcia, F. et al. The Synthesis of Thienopyrroles. Synthesis (1985) 143-156.

Hemetsberger, H. et al. Enazides, III: Thermolysis of alpha-Azido-cinnamates. Synthesis of Indol Carboxylates. Monatsh. Chem. (1970) 101(1):161-165.

Hemetsberger, H.; Knittel, D. Enazides, IV: Synthesis and Thermolysis of alpha-Azidoacrylates. Monatsh. Chem. (1972) 103(1):194-204.

Hughes, D.L. Progress in the Fischer Indole Reaction. A. Review. Org. Prep. Proced. Int. (1993) 25(6):607-632.

Ketcha, D.M. Five-Membered Ring Systems: Pyrroles and Benzo Derivatives. Prog. Heterocycl. Chem. (1999) 11:124-14.

Love, B.E.; Nguyen, B.T. A General Synthesis of 1-(Dialkylaminomethyl)indoles. Synlett (1998) :1123-1125.

Martinez, S.J.; Joule, J.A. The Synthesis of 2,3,4,6-Tetrahydro-5-hydroxy-2,6-dimethyl-1H-pyrido-[4,3-b]carbazole; Attempts to Synthesise 2,3,4,10-Tetrahydro-5-hydroxy-2-methyl-1H-pyrido[3,4-b]carbazole. J. Chem. Soc., Perkin Trans. 1 (1979) 3155-3160.

Monge, A. et al. Selective Thromboxane Synthetase Inhibitors and Antihypertensive Agents. New Derivatives of 4-Hydrazino-5H-pyridazino[4,5-b]indole, 4-Hydrazinopyridazino[4,5-a]indole, and Related Compounds. J. Med. Chem. (1987) 30:1029-1035.

Murakami, Y. et al. p-Toluenesulfonic Acid and Cation Exchange Resin in Aprotic Solvent: Valuable Catalysts for Fischer Indolization. Heterocycles (1984) 22(5):1211-1216.

Nagarathnam, D.; Johnson, M.E. A New Synthesis of 5-Bromo-DL-tryptophan. Synth. Commun. (1993) 23(14):2011-2017.

Nakamura, T. et al. Molecular Cloning and Characterization of a New Human Histamine Receptor, HH4R Biochem. Biophys. Res. Commun. (2000) 279:615-620.

Phillips, M.A. The Formation of 2-Substituted Benziminazoles. J. Chem. Soc. (1928) :2393-2399.

Preston, P.N. Synthesis, Reactions, and Spectroscopic Properties of Benzimidazoles. Chem. Rev. (1974) 74(3):279-314.

Rastogi, R.; Sharma, S. Synthesis of 2-Substituted Benzofurans as Potential Anthelmintics. Indian J. Chem. (1982) 21B:485-487.

Romero, D.L. et al. Bis(heteroaryl)piperazine (BHAP) Reverse Transcriptase Inhibitors: Structure-Activity Relationships of Novel Substituted Indole Analogues and the Identification of 1-[(5-Methanesulfonamido-1H-indol-2yl)-carbonyl]-4-[3-[(1-methylethyl)amino]-pyridinyl]piperazine Monomethanesulfonate (U-90152S), a Second-Generation Clinical Candidate. J. Med. Chem. (1993) 36(10):1505-1508.

Romero, D.L. et al. Discovery, Synthesis, and Bioactivity of Bis(heteroaryl)piperazines. 1. A Novel Class of Non-Nucleoside HIV-1 Reverse Transcriptase Inhibitors. J. Med. Chem. (1994) 37(7):999-1014.

Romero, D.L. et al. Targeting Delavirdine/Atevirdine Resistant HIV-1: Identification of (Alkylamino)piperidine-Containing Bis(heteroaryl)piperazines as Broad Spectrum HIV-1 Reverse Transcriptase Inhibitors. J. Med. Chem. (1996) 39(19):3769-3789.

Salituro, F.G. et al. 3-(2-Carboxyindol-3-yl)propionic Acid Derivatives: Antagonists of the Strychnine-Insensitive Gylcine Receptor Associated with the N-Methyl-D-aspartate Receptor Complex. J. Med. Chem. (1990) 33(11):2944-2946 This was listed incorrectly under King, F.D. in 1599 IDS 1st supplement.

Shafiee, A. et al. Synthesis and Local Anesthetic Activity of Benzo[b]furan Derivatives. J. Pharm. Sci. (1978) 67(1):125-127.

Sundberg, R.J.; Russell, H.F. Syntheses with N-Protected 2-Lithioindoles. J. Org. Chem. (1973) 38(19):3324-333.

Suzuki, H. et al. Unexpected Formation of Quinolone Dervatives in Reissert Indole Synthesis. Synlett (2000) 8:1196-1198.

Tani, M. et al. Regioselective and Non-reductive C3-Debromination of Indole Nucleus. Synlett (1996) 9:931-932.

Yamada, F.; Somei, M. A Convenient Synthetic Approach to 4-Substituted Indoles. Heterocycles (1987) 26(5):1173-1176.

Chemical Abstracts, vol. 78, No. 15, Apr. 16, 1973 Columbus, Ohio, Burov, Yu. V. et al.: "Derivatives of benzofuran-2-carboxylic acids and their action on the central nervous system." XP002210361.

Chemical Abstracts, vol. 130, No. 4, Jan. 25, 1999, Columbus, Ohio, Chang, Mayland et al., "Absorption, distribution, metabolism, and excretion of atevirdine in the rat." XP002210368.

Siavosh Mahboobi et al., "Synthetic 2-aroylindole derivatives as a new class of potent tubulin-inhibitory, antimitotic agents" Journal of Medicinal Chemistry, vol. 44, No. 26, 2001 pp. 4535-4553 XP002210359.

Chemical Abstracts, vol. 127, No. 3, Jul. 21, 1997 Columbus, Ohio, Takashima, Junko: "Preparation of benzofuran derivatives as antihypertensive agents" XP002210363.

Chemical Abstracts, vol. 121, No. 19, Nov. 7, 1994, Columbus, Ohio, Zawadowski, Teodor et al., "Synthesis of piperazinamides of benzofuran-2-and-3-carboxylic acids." XP002210364 & Abstract ACTA Pol. Pharm., vol. 50, No. 6 1993 pp. 457-459 & Database CAPLUS Online Chemical Abstract Service, Columbus, Ohio XP002210369.

Chemical Abstracts, vol. 119, No. 3, Jul. 19, 1993 Columbus, Ohio, Shibayama, Katsuhiro et al., "Preparation of piperazine or piperidine group-containing indoles and their use as anti-inflammatory, antiallergy, and anti-PAF agents." XP002210365 & JP 09325131 Toray Industries Dec. 16, 1997 & Database CAPLUS Online Chemical Abstract Service, Columbus, Ohio, XP002210370.

Chemical Abstracts, vol. 111, No. 19, Nov. 6, 1989, Columbus, Ohio, Komoto, Teruo et al., "Preparation of (indolylcarbonyl) piperazines as platelet aggregation inhibitors." XP002210366 & JP 89132579 S.S. Pharmaceutical Co., Ltd. May 25, 1989 & Database CAPLUS Online Chemical Abstracts Service, Columbus, Ohio XP002210371.

Chemical Abstracts, "Derivatives of benzofluran-2-carboxylic acids and their action on the central nervous system" XP-002210367.

Ennis, B.C. et al. 2-Trihalogenomethylbenzazoles. Part III. Reactions of 2-Trichloromethylbenzimidazole with Nucleophiles. J. Chem. Soc. C (1967) 1:30-33.

Crank, G. and A. Mursyidi. Photochemistry of Heterocyclics. III. Photolysis of Various 2-Substituted Benzimidazoles. Aust. J. Chem. (1982) 35:775-784.

Jablonowski, J. A. et al. The First Potent and Selective Non-Imidazole Human Histamine H4 Receptor Antagonists. J. Med. Chem. (2003) 46(19):3957-3960.

Gantner, F. et al. Histamine H4 and H2 Receptors Control Histamine-Induced Interleukin-16 Release from Human CD8+ T Cells. J. Pharmacol. Exp. Ther. (2002) 303(1):300-307.

Shin, N. et al. Molecular Modeling and Site-Specific Mutagenesis of the Histamine-Binding Site of the Histamine H4 Receptor. Mol. Pharmacol. (2002) 62(1):38-47.

Hashimoto, T. et al. A Selective Human H(4)-Receptor Agonist: (-)-2-Cyano-1-methyl-3-((2R,5R)-5-[1H-imidazol-4(5)-yl]tetrahydrofuran-2-yl)methylguanidine. J. Med. Chem. (2003) 46(14):3162-3165.

Harusawa, S. Synthesis of (±)-trans- or cis-(5-Aminomethyltetrahydrofuranyl)imidazole by Mitsunobu Cyclization: Synthetic Studies toward Novel Histamine H3 or H4-Ligands. Chem. Pharm. Bull. (2003) 51(3):325-329.

Harusawa, S. et al. Efficient Synthesis of trans- or cis-4(5)-(5-Aminomethyltetrahydrofuran-2-yl)imidazoles via Diazafulvene Intermediates: Synthetic Approach toward Human Histamine H4-Ligands. Chem. Pharm. Bull. (2003) 51(7):832-837.

O'Reilly, M. et. Al. Identification of a histamine H4 receptor on human eosinophils-role in eosinophil chemotaxis. Journal of Receptors and Signal Transduction (2002) 22(1-4):431-448.

Arrang, J.-M. et al. Auto-inhibition of Brain Histamine Release Mediated by a Novel Class (H3) of Histamine Receptor. Nature (1983) 302:832-837.

Ash, A.S.F.; Schild, H.O. Receptors Mediating Some Actions of Histamine. Br. J. Pharmac. Chemother. (1966) 27:427-439.

Barger, G.; Dale, H.H. Chemical Structure and Sympathomimetic Action of Amines. J. Physiol. (1910) 41:19-59 Reprinted in Adventures in Physiology; Sir Henry H. Dale, Ed.; The Wellcome Trust: London, 1965; pp. 67-98.

Black, J.W. et al. Definition and Antagonism of Histamine H2-Receptors. Nature (1972) 236:385-390.

Gantz, I. et al. Molecular Cloning of a Gene Encoding the Histamine H2 Receptor. Proc. Natl. Acad. Sci. USA (1991) 88:429-433.

Hill, S.J. et al. International Union of Pharmacology. XIII. Classification of Histamine Receptors. Pharmacol. Rev. (1997) 49(3):253-278.

Liu, C. et al. Cloning and Pharmacological Characterization of a Fourth Histamine Receptor (H4) Expressed in Bone Marrow. Mol. Pharmacol. (2001) 59(3):420-426.

Lovenberg, T.W. et al. Cloning and Functional Expression of the Human Histamine H3 Receptor. Mol. Pharmacol. (1999) 55(6):1101-1107.

Morse, K.L. et al. Cloning and Characterization of a Novel Human Histamine Receptor. J. Pharmacol. Exp. Ther. (2001) 296(3):1058-1066.

Nguyen, T. et al. Discovery of a Novel Member of the Histamine Receptor Family. Mol. Pharmacol. (2001) 59(3):427-433.

Oda, T. et al. Molecular Cloning and Characterization of a Novel Type of Histamine Receptor Preferentially Expressed in Leukocytes. J. Biol. Chem. (2000) 275(47):36781-36786.

Raible, D.G. et al. Pharmacologic Characterization of a Novel Histamine Receptor on Human Eosinophils. Am. J. Respir. Crit. Care Med. (1994) 149:1506-1511.

Yamashita, M. et al. Expression Cloning of a cDNA Encoding the Bovine Histamine H1 Receptor. Proc. Natl. Acad. Sci. USA (1991) 88:11515-11519.

Zhu, Y. et al. Cloning, Expression, and Pharmacological Characterization of a Novel Human Histamine Receptor. Mol. Pharmacol. (2001) 59(3):434-441.

Bigge, C.F. et al. New Preparations of the N-Methyl-D-Aspartate Receptor Antagonist, 4-(3-Phosphonopropyl)-2-Piperazinecarboxylic Acid. Tetrahedron Lett. (1989) 30(39):5193-5196.

Dubey R. et al., "Mass Spectral Studies of 2,5-Disubstituted Benzimidazoles", *Indian Journal of Chemistry, Section B*, (1987) vol. 26, No. 4, pp. 395-297.

HETEROCYCLIC COMPOUNDS

FIELD OF THE INVENTION

The invention relates to novel, pharmaceutically active, fused heterocyclic compounds and methods of using them to treat or prevent disorders and conditions mediated by the histamine $H_4$ receptor.

BACKGROUND OF THE INVENTION

Histamine was first identified as a hormone (G. Barger and H. H. Dale, *J. Physiol.* (*London*) 1910, 41:19-59) and has since been demonstrated to play a major role in a variety of physiological processes, including the inflammatory "triple response" via $H_1$ receptors (A. S. F. Ash and H. O. Schild, *Br. J. Pharmac. Chemother.* 1966, 27:427-439), gastric acid secretion via $H_2$ receptors (J. W. Black et al., *Nature* 1972, 236:385-390), and neurotransmitter release in the central nervous system via $H_3$ receptors (J.-M. Arrang et al., *Nature* 1983, 302:832-837) (for review see S. J. Hill et al., *Pharmacol. Rev.* 1997, 49(3):253-278). All three histamine receptor subtypes have been demonstrated to be members of the superfamily of G protein-coupled receptors (I. Gantz et al., *Proc. Natl. Acad. Sci. U.S.A.* 1991, 88:429-133; T. W. Lovenberg et al., *Mol. Pharmacol.* 1999, 55(6):1101-1107; M. Yamashita et al., *Proc. Natl. Acad. Sci. U.S.A.* 1991, 88:11515-11519). There are, however, additional functions of histamine that have been reported, for which no receptor has been identified. For example, in 1994, Raible et al. demonstrated that histamine and R-α-methylhistamine could activate calcium mobilization in human eosinophils (D. G. Raible et al., *Am. J. Respir. Crit. Care Med.* 1994, 149:1506-1511). These responses were blocked by the $H_3$-receptor antagonist thioperamide. However, R-α-methylhistamine was significantly less potent than histamine, which was not consistent with the involvement of known $H_3$ receptor subtypes. Therefore, Raible et al. hypothesized the existence of a novel histamine receptor on eosinophils that was non-$H_1$, non-$H_2$, and non-$H_3$. Most recently several groups (T. Oda et al., *J. Biol. Chem.* 2000, 275(47):36781-36786; C. Liu et al., *Mol. Pharmacol.* 2001, 59(3):420-426; T. Nguyen et al., *Mol. Pharmacol.* 2001, 59(3):427-433; Y. Zhu et al., *Mol. Pharmacol.* 2001, 59(3):434-441; K. L. Morse et al., *J. Pharmacol. Exp. Ther.* 2001, 296(3):1058-1066) have identified and characterized a fourth histamine receptor subtype, the $H_4$ receptor. This receptor is a 390 amino acid, seven-transmembrane, G protein-coupled receptor with approximately 40% homology to the histamine $H_3$ receptor. In contrast to the $H_3$ receptor, which is primarily located in the brain, the $H_4$ receptor is expressed at greater levels in neutrophils and mast cells, among other cells, as reported by Morse et al. (see above).

Events that elicit the inflammatory response include physical stimulation (including trauma), chemical stimulation, infection, and invasion by a foreign body. The inflammatory response is characterized by pain, increased temperature, redness, swelling, reduced function, or a combination of these. Many conditions, such as allergies, asthma, chronic obstructed pulmonary disease (COPD), atherosclerosis, and autoimmune diseases, including rheumatoid arthritis and lupus, are characterized by excessive or prolonged inflammation. Inhibition of leukocyte recruitment can provide significant therapeutic value. Inflammatory diseases or inflammation-mediated diseases or conditions include, but are not limited to, acute inflammation, allergic inflammation, and chronic inflammation.

Mast cell de-granulation (exocytosis) leads to an inflammatory response that may be initially characterized by a histamine-modulated wheal and flare reaction. A wide variety of immunological (e.g., allergens or antibodies) and non-immunological (e.g., chemical) stimuli may cause the activation, recruitment, and de-granulation of mast cells. Mast cell activation initiates allergic ($H_1$) inflammatory responses, which in turn cause the recruitment of other effector cells that further contribute to the inflammatory response. The histamine H2 receptors modulate gastric acid secretion, and the histamine H3 receptors affect neurotransmitter release in the central nervous system.

Examples of textbooks on the subject of inflammation include J. I. Gallin and R. Snyderman, *Inflammation: Basic Principles and Clinical Correlates*, 3$^{rd}$ Edition, (Lippincott Williams & Wilkins, Philadelphia, 1999); V. Stvrtinova, J. Jakubovsky and I. Hulin, "Inflammation and Fever", *Pathophysiology Principles of Diseases* (Textbook for Medical Students, Academic Press, 1995); Cecil et al., *Textbook Of Medicine*, 18$^{th}$ Edition (W. B. Saunders Company, 1988); and Steadmans Medical Dictionary.

SUMMARY OF THE INVENTION

The invention features a compound of formula (I):

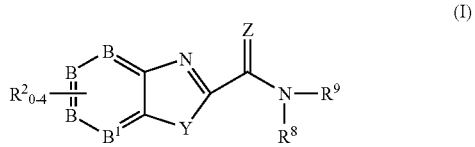

wherein
B and $B^1$ are C or up to one of B and $B^1$ may be N;
Y is O, S or NH;
Z is O, S or $NR^z$, where $R^z$ is H or $C_{1-4}$alkyl;
$R^8$ is H and $R^9$ is

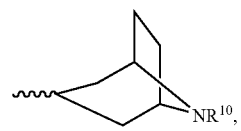

where $R^{10}$ is H or $C_{1-4}$alkyl, or
$R^8$ and $R^9$ are taken together with their N of attachment to form

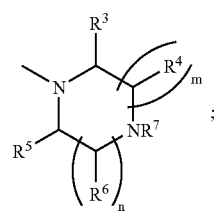

n is 1 or 2;
m is 1 or 2;
n+m is 2 or 3;
$R^2$ are, independently, H, F, Cl, Br, I, $C_{1-4}$alkyl, $C_{1-4}$alkoxy, —$C_{3-6}$cycloalkyl, —$OC_{3-6}$cycloalkyl, —$OCH_2Ph$, —CF$_3$, —OCF$_3$, —SCF$_3$, —OH, —(C=O)R$^k$ (wherein R$^k$ is H, C$_{1-4}$alkyl, —OH, phenyl, benzyl, phenethyl or C$_{1-6}$alkoxy), —(N—R$^t$)(C=O)R$^k$ (where R$^t$ is H or C$_{1-4}$alkyl), —(N—R$^t$)SO$_2$C$_{1-4}$alkyl, —(S=(O)$_p$)—C$_{1-4}$ alkyl (wherein p is 0, 1 or 2), nitro, —NR$^l$R$^m$ (wherein R$^l$ and R$^m$ are independently selected from H, C$_{1-4}$alkyl, phenyl, benzyl or phenethyl, or R$^l$ and R$^m$ taken together with the nitrogen to which they are attached, form a 4-7 membered heterocyclic ring with 0 or 1 additional heteroatoms selected from O, S, NH or NC$_{1-4}$alkyl), —SO$_2$NR$^l$R$^m$, —(C=O)NR$^l$R$^m$, cyano or phenyl, where any phenyl or alkyl or cycloalkyl moiety of the foregoing is optionally and independently substituted with between 1 and 3 substituents selected from C$_{1-3}$alkyl, halo, hydroxy, amino, and C$_{1-3}$alkoxy;

R$^3$ and R$^4$ are, independently, H, C$_{1-4}$alkyl, C$_{3-6}$cycloalkyl, C$_{1-4}$alkyl(C$_{3-6}$cycloalkyl), cyano, —CF$_3$, —(CO)NR$^p$R$^q$, —(CO)OR$^r$, —CH$_2$NR$^p$R$^q$ or —CH$_2$OR$^r$; where R$^p$, R$^q$ and R$^r$ are independently selected from H, C$_{1-4}$alkyl, C$_{3-6}$cycloalkyl, phenyl, —C$_{1-2}$alkyl(C$_{3-6}$cycloalkyl), benzyl or phenethyl, or R$^p$ and R$^q$ taken together with the nitrogen to which they are attached, form a 4-7 membered heterocyclic ring with 0 or 1 additional heteroatoms selected from O, S, NH or NC$_{1-6}$alkyl, and where any phenyl or alkyl or cycloalkyl moiety of the foregoing is optionally and independently substituted with between 1 and 3 substituents selected from C$_{1-3}$alkyl, halo, hydroxy, amino, and C$_{1-3}$alkoxy;

R$^5$ and R$^6$ are, independently, H or C$_{1-6}$alkyl;

R$^7$ is —R$^a$, —R$^b$R$^a$, —R$^e$—O—R$^a$ or —R$^e$—N(R$^c$)(R$^d$), where R$^a$ is H, cyano, —(C=O)N(R$^c$)(R$^d$), —C(=NH)(NH$_2$), C$_{1-10}$alkyl, C$_{2-8}$alkenyl, C$_{3-8}$cycloalkyl, C$_{4-7}$heterocyclic radical or phenyl, where the C$_{4-7}$heterocyclic radical is attached at a carbon atom and contains one of O, S, NH or NC$_{1-4}$alkyl, and optionally an additional NH or NC$_{1-6}$alkyl in rings of 5 or 6 or 7 members, where R$^b$ is C$_{1-8}$alkylene or C$_{2-8}$alkenylene, where R$^e$ is C$_{2-8}$alkylene or C$_{2-8}$alkenylene, where R$^c$ and R$^d$ are each independently H, C$_{1-4}$alkyl, C$_{2-4}$alkenyl, C$_{3-6}$cycloalkyl or phenyl, or R$^c$ and R$^d$ taken together with the nitrogen to which they are attached, form a 4-7 membered heterocyclic ring with 0 or 1 additional heteroatoms selected from O, S, NH or NC$_{1-6}$alkyl, and where any phenyl or alkyl or cycloalkyl moiety of the foregoing is optionally and independently substituted with between 1 and 3 substituents selected from C$_{1-3}$alkyl, halo, hydroxy, amino, and C$_{1-3}$alkoxy;

alternatively, R$^7$ may be taken together with an adjacent R$^4$ as well as their carbon and nitrogen of attachment to form a 5, 6 or 7 membered heterocyclic ring, with 0 or 1 additional heteroatoms selected from O, S, NH or NC$_{1-6}$alkyl, and optionally and independently substituted with between 1 and 3 substituents selected from C$_{1-3}$alkyl, halo, hydroxy, amino, and C$_{1-3}$alkoxy; and enantiomers, diastereomers and pharmaceutically acceptable salts and esters thereof, with the following provisos, that R$^6$ adjacent to N must be H where R$^4$ adjacent to N is other than H, and that R$^2$ cannot be benzoyl when one of R$^4$ and R$^6$ is methyl and the other is hydrogen.

The invention also features pharmaceutical compositions containing such compounds and methods of using such compositions in the treatment or prevention of H$_4$-mediated diseases and conditions, particularly those wherein it is desirable to antagonize the H$_4$ receptor.

DETAILED DESCRIPTION

Preferably, B and B$^1$ are C or B$^1$ may be N.
Most preferably, B and B$^1$ are C.
Preferably, Y is NH.
Preferably, Z is O.
Preferably, R$^{10}$ is H or methyl.
Preferably, n is 1 and m is 1.
Preferably, R$^2$ are, independently, selected from the group consisting of H, —F, —Cl, —Br, —I, —CH$_3$, —CH$_2$CH$_3$, —OCH$_3$, —OCH$_2$CH$_3$, —OCH(CH$_3$)$_2$, cyclopropyl, cyclobutyl, cyclopentyl, cyclohexyl, —Ocyclopentyl, —Ocyclohexyl, —CF$_3$, —OCF$_3$, —SCF$_3$, —C(O)CH$_3$, —C(O)CH$_2$CH$_3$, —OH, —COOH, —C(O)phenyl, —C(O)benzyl, —COOCH$_3$, —COOCH$_2$CH$_3$, —NHCOCH$_3$, —NCH$_3$COCH$_3$, —NHSO$_2$CH$_3$, —NCH$_3$SO$_2$CH$_3$, —SOCH$_3$, —SO$_2$CH$_3$, —NO$_2$, —NH$_2$, —NHCH$_3$, —N(CH$_3$)$_2$, —N(CH$_2$CH$_3$)$_2$, -pyrrolidin-1-yl, -imidazolidin-1-yl, -pyrazolidin-1-yl, -piperidin-1-yl, -piperazin-1-yl, -morpholin-4-yl, -thiomorpholin-4-yl, —SO$_2$NH$_2$, —SO$_2$NHCH$_3$, —SO$_2$N(CH$_3$)$_2$, —SO$_2$N(CH$_2$CH$_3$)$_2$, —SO$_2$pyrrolidin-1-yl, —SO$_2$imidazolidin-1-yl, —SO$_2$pyrazolidin-1-yl, —SO$_2$piperidin-1-yl, —SO$_2$piperazin-1-yl, —SO$_2$morpholin-4-yl, —SO$_2$thiomorpholin-4-yl, —C(O)NH$_2$, —C(O)N(CH$_3$)$_2$, —C(O)NH(CH$_3$), —C(O)N(CH$_2$CH$_3$)$_2$, —C(O)pyrrolidin-1-yl, —C(O)imidazolidin-1-yl, —C(O)pyrazolidin-1-yl, —C(O)piperidin-1-yl, —C(O)piperazin-1-yl, —C(O)morpholin-4-yl, —C(O)thiomorpholin-4-yl, —CN and phenyl.

Most preferably, R$^2$ are, independently, selected from the group consisting of hydrogen, methyl, trifluoromethyl, methoxy, trifluoromethoxy, nitro, chloro, fluoro and benzoyl. Further, it is most preferred that one or two of R$^2$ are not hydrogen.

Preferably, R$^3$ and R$^4$ are, independently, selected from the group consisting of a) H, b) —CH$_3$, —CH$_2$CH$_3$, —CH$_2$CH$_2$CH$_3$, —CH(CH$_3$)$_2$, n-butyl, i-butyl, t-butyl, c) cyclopropyl, cyclopentyl, cyclohexyl, —CH$_2$cyclopropyl, —CH$_2$cyclopentyl, —CH$_2$cyclohexyl, —CH$_2$Ocyclopropyl, —CH$_2$Ocyclopentyl, —CH$_2$Ocyclohexyl, d) cyano, e) trifluoromethyl, f) —(C=O)NH$_2$, —(C=O)NHC$_{1-4}$alkyl, —(C=O)N(C$_{1-4}$alkyl)$_2$, —(C=O)NHphenyl, —(C=O)pyrrolidin-1-yl, —(C=O)imidazolidin-1-yl, —(C=O)pyrazolidin-1-yl, —(C=O)piperidin-1-yl, —(C=O)piperazin-1-yl, —(C=O)morpholin-4-yl, —(C=O)thiomorpholin-4-yl, g) —COOH, —COOCH$_3$, —COOCH$_2$CH$_3$, —COOphenyl, —COObenzyl, h) —CH$_2$NH$_2$, —CH$_2$NHC$_{1-4}$alkyl, —CH$_2$N(C$_{1-4}$alkyl)$_2$, —CH$_2$NHphenyl, —CH$_2$NHbenzyl, —CH$_2$pyrrolidin-1-yl, —CH$_2$imidazolidin-1-yl, —CH$_2$pyrazolidin-1-yl, —CH$_2$piperidin-1-yl, —CH$_2$piperazin-1-yl, —CH$_2$morpholin4-yl, —CH$_2$thiomorpholin-4-yl, i) —CH$_2$OH, —CH$_2$CH$_2$OH, —CH$_2$CH$_2$CH$_2$OH, —CH$_2$OCH$_3$, —CH$_2$OCH$_2$CH$_3$, —CH$_2$OCH$_2$CH$_2$CH$_3$, —CH$_2$OCH(CH$_3$)$_2$, —CH$_2$O-n-butyl, —CH$_2$O-1-butyl, —CH$_2$O-t-butyl, —CH$_2$Ophenyl, —CH$_2$Obenzyl and —CH$_2$OCH$_2$cyclopropyl.

Most preferably, R$^3$ and R$^4$ are, independently, H or —CH$_3$.

Preferably, R$^5$ and R$^6$ are, independently, selected from the group consisting of H and methyl.

Most preferably, R$^5$ and R$^6$ are H.

Preferably, $R^7$ is selected from the group consisting of
a) H, —$CH_2CH_2OH$, —$CH_2CH_2CH_2OH$,
b) cyano,
c) —(C=O)$NH_2$, —(C=O)$NHC_{1-4}$alkyl, —(C=O)N$(C_{1-4}$alkyl$)_2$, —(C=O)NHphenyl, —(C=O)pyrrolidin-1-yl, —(C=O)imidazolidin-1-yl, —(C=O)pyrazolidin-1-yl, —(C=O)piperidin-1-yl, —(C=O)piperazin-1-yl, —(C=O)morpholin-4-yl, —(C=O)thiomorpholin-4-yl, —$CH_2$(C=O)$NH_2$, —$CH_2$(C=O)$NHC_{1-4}$alkyl, —$CH_2$(C=O)N($C_{1-4}$alkyl$)_2$, —$CH_2$(C=O)NHphenyl, —$CH_2$(C=O)pyrrolidin-1-yl, —$CH_2$(C=O)imidazolidin-1-yl, —$CH_2$(C=O)pyrazolidin-1-yl, —$CH_2$(C=O)piperidin-1-yl, —$CH_2$(C=O)piperazin-1-yl, —$CH_2$(C=O)morpholin4-yl, —$CH_2$(C=O)thiomorpholin-4-yl, —$CH_2CH_2O$(C=O)$NH_2$, —$CH_2CH_2O$(C=O)$NHC_{1-4}$alkyl, —$CH_2CH_2O$(C=O)N($C_{1-4}$alkyl$)_2$, —$CH_2CH_2O$(C=O)NHphenyl, —$CH_2CH_2O$(C=O)pyrrolidin-1-yl, —$CH_2CH_2O$(C=O)imidazolidin-1-yl, —$CH_2CH_2O$(C=O)pyrazolidin-1-yl, —$CH_2CH_2O$(C=O)piperidin-1-yl, —$CH_2CH_2O$(C=O)piperazin-1-yl, —$CH_2CH_2O$(C=O)morpholin-4-yl, —$CH_2CH_2O$(C=O)thiomorpholin4-yl,
d) —C(=NH)($NH_2$), —$CH_2$C(=NH)($NH_2$),
e) —$CH_3$, —$CH_2CH_3$, —$CH_2CH_2CH_3$, —CH($CH_3$)$_2$, n-butyl, i-butyl, t-butyl, —$CH_2CH_2OCH_3$, —$CH_2CH_2OCH_2CH_3$, —$CH_2CH_2OCH_2CH_2CH_3$, —$CH_2CH_2OCH(CH_3)_2$, —$CH_2CH_2O$-n-butyl, —$CH_2CH_2O$-1-butyl, —$CH_2CH_2O$-t-butyl,
f) —CH=$CH_2$, —$CH_2$CH=$CH_2$,
g) cyclopropyl, cyclopentyl, cyclohexyl, —$CH_2$cyclopropyl, —$CH_2$cyclopentyl, —$CH_2$cyclohexyl, —$CH_2CH_2O$cyclopropyl, —$CH_2CH_2O$cyclopentyl, —$CH_2CH_2O$cyclohexyl,
h) pyrrolidinyl, imidazolidinyl, pyrazolidinyl, piperidinyl, piperazinyl, morpholinyl, thiomorpholinyl, —$CH_2$pyrrolidinyl, —$CH_2$imidazolidinyl, —$CH_2$pyrazolidinyl, —$CH_2$piperidinyl, —$CH_2$piperazinyl, —$CH_2$morpholinyl, —$CH_2$thiomorpholinyl,
i) —$CH_2CH_2NH_2$, —$CH_2CH_2NHC_{1-4}$alkyl, —$CH_2CH_2N(C_{1-4}$alkyl$)_2$, —$CH_2CH_2$NHphenyl, —$CH_2CH_2$pyrrolidin-1-yl, —$CH_2CH_2$imidazolidin-1-yl, —$CH_2CH_2$pyrazolidin-1-yl, —$CH_2CH_2$piperidin-1-yl, —$CH_2CH_2$piperazin-1-yl, —$CH_2CH_2$morpholin-4-yl, —$CH_2CH_2$thiomorpholin-4-yl,
j) phenyl, benzyl, phenethyl and benzyloxymethyl.

Most preferably, $R^7$ is selected from the group consisting of H, —$CH_3$ and —$CH_2CH_3$.

Preferred $R^7$ taken together with an adjacent $R^4$ as well as their carbon and nitrogen of attachment are pyrrolidin-1,2-yl, imidazolidin-1,2-yl, imidazolidin-1,5-yl, pyrazolidin-1,5-yl, piperidin-1,2-yl, piperazin-1,2-yl, morpholin-4,5-yl and thiomorpholin-4,5-yl.

Most preferred $R^7$ taken together with an adjacent $R^4$ as well as their carbon and nitrogen of attachment are pyrrolidin-1,2-yl and piperidin-1,2-yl.

The "pharmaceutically acceptable salts and esters thereof" refer to those salt and ester forms of the compounds of the present invention that would be apparent to the pharmaceutical chemist, i.e., those that are non-toxic and that would favorably affect the pharmacokinetic properties of said compounds of the present invention. Those compounds having favorable pharmacokinetic properties would be apparent to the pharmaceutical chemist, i.e., those that are non-toxic and that possess such pharmacokinetic properties to provide sufficient palatability, absorption, distribution, metabolism and excretion. Other factors, more practical in nature, that are also important in the selection are cost of raw materials, ease of crystallization, yield, stability, hygroscopicity, and flowability of the resulting bulk drug. In addition, acceptable salts of carboxylates include sodium, potassium, calcium and magnesium. Examples of suitable cationic salts include hydrobromic, hydroiodic, hydrochloric, perchloric, sulfuric, maleic, fumaric, malic, tartatic, citric, benzoic, mandelic, methanesulfonic, hydroethanesulfonic, benzenesulfonic, oxalic, pamoic, 2-naphthalenesulfonic, p-toluenesulfonic, cyclohexanesulfamic and saccharic. Examples of suitable esters include such esters where one or more carboxyl substituents is replaced with p-methoxybenzyloxycarbonyl, 2,4,6-trimethylbenzyloxycarbonyl, 9-anthryloxycarbonyl, $CH_3SCH_2COO$—, tetrahydrofur-2-yloxycarbonyl, tetrahydropyran-2-yloxycarbonyl, fur-2-uloxycarbonyl, benzoylmethoxycarbonyl, p-nitrobenzyloxycarbonyl, 4-pyridylmethoxycarbonyl, 2,2,2-trichloroethoxycarbonyl, 2,2,2-tribromoethoxycarbonyl, t-butyloxycarbonyl, t-amyloxycarbonyl, diphenylmethoxycarbonyl, triphenylmethoxycarbonyl, adamantyloxycarbonyl, 2-benzyloxyphenyloxycarbonyl, 4-methylthiophenyloxycarbonyl, or tetrahydropyran-2-yloxycarbonyl.

The provisos are based on a failure to find activity in at least one compound meeting the specifications of each proviso.

Preferred compounds of Formula I were made as described in Examples 1-45 and Schemes 14, and are selected from the group consisting of:

| EX | COMPOUND |
|---|---|
| 1 | (1H-Benzoimidazol-2-yl)-(4-methyl-piperazin-1-yl)-methanone; |
| 2 | (1H-Benzoimidazol-2-yl)-(4-ethyl-piperazin-1-yl)-methanone; |
| 3 | (1H-Benzoimidazol-2-yl)-(3-methyl-piperazin-1-yl)-methanone; |
| 4 | (1H-Benzoimidazol-2-yl)-(4-methyl-[1,4]diazepan-1-yl)-methanone; |
| 5 | 1H-Benzoimidazole-2-carboxylic acid (8-methyl-8-aza-bicyclo[3.2.1]oct-3-yl)-amide; |
| 6 | (5-Chloro-1H-benzoimidazol-2-yl)-(4-methyl-piperazin-1-yl)-methanone; |
| 7 | (5-Chloro-1H-benzoimidazol-2-yl)-piperazin-1-yl-methanone; |
| 8 | (5-Chloro-1H-benzoimidazol-2-yl)-(3-methyl-piperazin-1-yl)-methanone; |
| 9 | (5,6-Difluoro-1H-benzoimidazol-2-yl)-(4-methyl-piperazin-1-yl)-methanone; |
| 10 | (5,6-Difluoro-1H-benzoimidazol-2-yl)-(4-ethyl-piperazin-1-yl)-methanone; |
| 11 | (5,6-Difluoro-1H-benzoimidazol-2-yl)-(3-methyl-piperazin-1-yl)-methanone; |
| 12 | (5,6-Difluoro-1H-benzoimidazol-2-yl)-(4-methyl-[1,4]diazepan-1-yl)-methanone; |
| 13 | 5,6-Difluoro-1H-benzoimidazole-2-carboxylic acid (8-methyl-8-aza-bicyclo[3.2.1]oct-3-yl)-amide; |
| 14 | (6-Chloro-5-fluoro-1H-benzoimidazol-2-yl)-(4-methyl-piperazin-1-yl)-methanone; |
| 15 | (6-Chloro-5-fluoro-1H-benzoimidazol-2-yl)-piperazin-1-yl-methanone; |
| 16 | (6-Chloro-5-fluoro-1H-benzoimidazol-2-yl)-(4-methyl-[1,4]diazepan-1-yl)-methanone; |
| 17 | 6-Chloro-5-fluoro-1H-benzoimidazole-2-carboxylic acid (8-methyl-8-aza-bicyclo[3.2.1]oct-3-yl)-amide; |
| 18 | (5-Chloro-6-methyl-1H-benzoimidazol-2-yl)-(4-methyl-piperazin-1-yl)-methanone; |
| 19 | (5-Chloro-6-methyl-1H-benzoimidazol-2-yl)-piperazin-1-yl-methanone; |
| 20 | (4-Methyl-1H-benzoimidazol-2-yl)-(3-methyl-piperazin-1-yl)-methanone; |
| 21 | (4-Ethyl-piperazin-1-yl)-(4-methyl-1H-benzoimidazol-2-yl)-methanone; |
| 22 | (4-Methyl-1H-benzoimidazol-2-yl)-(4-methyl-piperazin-1-yl)-methanone; |
| 23 | (4-Methyl-1H-benzoimidazol-2-yl)-piperazin-1-yl-methanone; |
| 24 | 4-Methyl-1H-benzoimidazole-2-carboxylic acid (8-methyl-8-aza-bicyclo[3.2.1]oct-3-yl)-amide; |
| 25 | 5-Methyl-1H-benzoimidazole-2-carboxylic acid (8-methyl-8-aza-bicyclo[3.2.1]oct-3-yl)-amide; |
| 26 | (5-Methyl-1H-benzoimidazol-2-yl)-(4-methyl-piperazin-1-yl)-methanone; |

| EX | COMPOUND |
|---|---|
| 27 | (4-Methyl-piperazin-1-yl)-(5-trifluoromethyl-1H-benzoimidazol-2-yl)-methanone; |
| 28 | Piperazin-1-yl-(5-trifluoromethyl-1H-benzoimidazol-2-yl)-methanone; |
| 29 | (5-Fluoro-1H-benzoimidazol-2-yl)-(4-methyl-piperazin-1-yl)-methanone; |
| 30 | (4-Ethyl-piperazin-1-yl)-(5-fluoro-1H-benzoimidazol-2-yl)-methanone; |
| 31 | (5-Fluoro-1H-benzoimidazol-2-yl)-piperazin-1-yl-methanone; |
| 32 | (5-Fluoro-1H-benzoimidazol-2-yl)-(3-methyl-piperazin-1-yl)-methanone; |
| 33 | 5-Fluoro-1H-benzoimidazole-2-carboxylic acid (8-methyl-8-azabicyclo[3.2.1]oct-3-yl)-amide; |
| 34 | (3H-Imidazo[4,5-b]pyridin-2-yl)-(4-methyl-piperazin-1-yl)-methanone; |
| 35 | Benzooxazol-2-yl-(4-methyl-piperazin-1-yl)-methanone; |
| 36 | (7-Methyl-benzooxazol-2-yl)-(4-methyl-piperazin-1-yl)-methanone; |
| 37 | (5-Methyl-benzooxazol-2-yl)-(4-methyl-piperazin-1-yl)-methanone; |
| 38 | (4-Methyl-benzooxazol-2-yl)-(4-methyl-piperazin-1-yl)-methanone; |
| 39 | Benzothiazol-2-yl-(4-methyl-piperazin-1-yl)-methanone; |
| 40 | (5-Benzoyl-1H-benzoimidazol-2-yl)-(4-methyl-piperazin-1-yl)-methanone; |
| 41 | (4-Chloro-1H-benzoimidazol-2-yl)-(4-methyl-piperazin-1-yl)-methanone; |
| 42 | (4-Methyl-piperazin-1-yl)-(4-nitro-1H-benzoimidazol-2-yl)-methanone; |
| 43 | (4-Amino-1H-benzoimidazol-2-yl)-(4-methyl-piperazin-1-yl)-methanone; |
| 44 | (4-Isopropylamino-1H-benzoimidazol-2-yl)-(4-methyl-piperazin-1-yl)-methanone; and |
| 45 | C-(5-Chloro-1H-benzoimidazol-2-yl)-C-(4-methyl-piperazin-1-yl)-methyleneamine. |

Additional preferred compounds of Formula I were made according to synthetic methods outlined in Schemes 1-3 and are selected from the group consisting of:

| EX | COMPOUND |
|---|---|
| 46 | (4,6-Difluoro-1H-benzoimidazol-2-yl)-(4-methyl-piperazin-1-yl)-methanone; |
| 47 | (4-Methyl-piperazin-1-yl)-(5-nitro-1H-benzoimidazol-2-yl)-methanone; |
| 48 | (5-Fluoro-4-methyl-1H-benzoimidazol-2-yl)-(4-methyl-piperazin-1-yl)-methanone; and |
| 49 | (5-Bromo-1H-benzoimidazol-2-yl)-(4-methyl-piperazin-1-yl)-methanone. |

Other preferred compounds of Formula I are made according to the synthetic methods outlined in Schemes 1-3 and are selected from the group consisting of:

| EX | COMPOUND |
|---|---|
| 50 | (5,6-Dichloro-1H-benzoimidazol-2-yl)-(4-methyl-piperazin-1-yl)-methanone; |
| 51 | (4,5-Dimethyl-1H-benzoimidazol-2-yl)-(4-methyl-piperazin-1-yl)-methanone; |
| 52 | (5,6-Dimethyl-1H-benzoimidazol-2-yl)-(4-methyl-piperazin-1-yl)-methanone; |
| 53 | (5-Methoxy-1H-benzoimidazol-2-yl)-(4-methyl-piperazin-1-yl)-methanone; |
| 54 | (5-Chloro-benzooxazol-2-yl)-(4-methyl-piperazin-1-yl)-methanone; |
| 55 | (5-Fluoro-benzooxazol-2-yl)-(4-methyl-piperazin-1-yl)-methanone; |
| 56 | (6-Fluoro-benzooxazol-2-yl)-(4-methyl-piperazin-1-yl)-methanone; |
| 57 | (5,7-Difluoro-benzooxazol-2-yl)-(4-methyl-piperazin-1-yl)-methanone; |
| 58 | (4-Methyl-piperazin-1-yl)-(5-trifluoromethoxy-benzooxazol-2-yl)-methanone; |
| 59 | (5-Chloro-benzothiazol-2-yl)-(4-methyl-piperazin-1-yl)-methanone; and |
| 60 | (4-Methyl-piperazin-1-yl)-(5-trifluoromethyl-benzothiazol-2-yl)-methanone. |

The following terms are defined below, and by their usage throughout disclosure.

"Alkyl" includes straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. Alkyl does not include cycloalkyl.

"Alkenyl" includes straight chain and branched hydrocarbon radicals as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Alkenyl does not include cycloalkenyl.

"Alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and $SO_2$.

"Cycloalkyl" includes cyclopropyl, cyclobutyl, cyclopentyl, cyclohexyl, cycloheptyl, cyclooctyl, and so on.

"Halo" includes fluoro, chloro, bromo, and iodo, and preferably fluoro or chloro.

"Patient" or "subject" includes mammals such as humans and animals (dogs, cats, horses, rats, rabbits, mice, non-human primates) in need of observation, experiment, treatment or prevention in connection with the relevant disease or condition. Preferably, the patient is a human.

"Composition" includes a product comprising the specified ingredients in the specified amounts as well as any product that results directly or indirectly from combinations of the specified ingredients in the specified amounts.

The compounds as described above may be made according to processes within the skill of the art and/or that are described in the schemes and examples that follow. To obtain the various compounds herein, starting materials may be employed that carry the ultimately desired substituents though the reaction scheme with or without protection as appropriate. Alternatively, it may be necessary to employ, in the place of the ultimately desired substituent, a suitable group that may be carried through the reaction scheme and replaced as appropriate with the desired substituent.

SCHEME 1

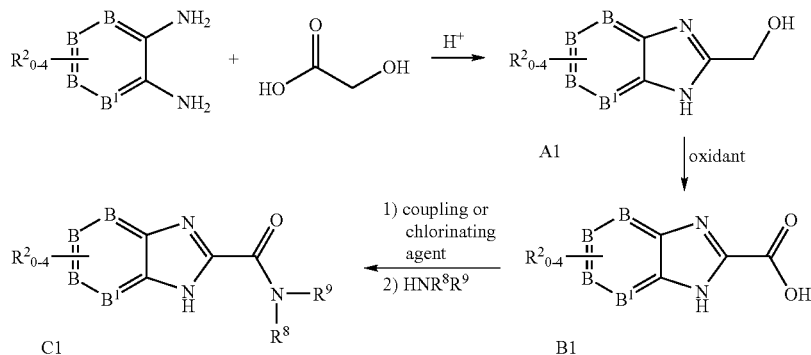

Referring to Scheme 1, there are disclosed the following notes and additions. The starting materials and $HNR^8R^9$ are commercially available or their synthesis is within the skill of the art.

SCHEME 2

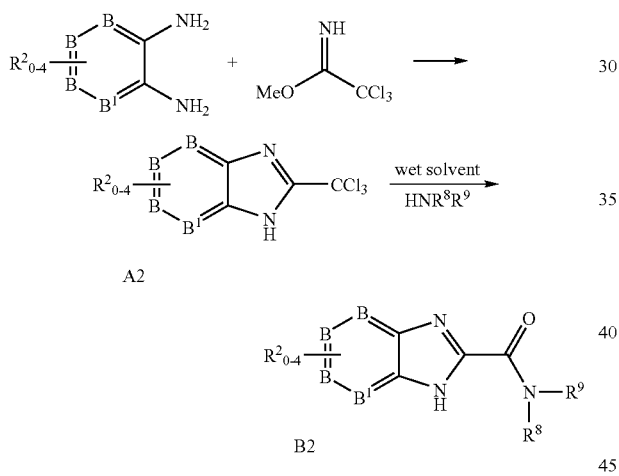

Referring to Scheme 2, there are disclosed the following notes and additions. The starting materials and $HNR^8R^9$ are commercially available or their synthesis is within the skill of the art. Starting materials are condensed to produce benzimidazole A2. The chlorine atoms of benzimidazole A2 are replaced by condensation with the secondary amine with concomitant hydrolysis resulting in formation of compound B2. Good yields of compound B2 may be obtained where a mild aqueous base is used in the condensation and hydrolysis reactions. Suitable mild aqueous bases are $2N\ K_2CO_3$, $2N\ NaHCO_3$, $0.1N\ NaOH$, etc.

SCHEME 3

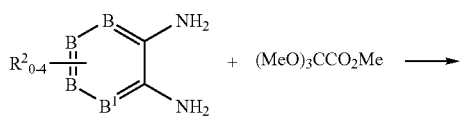

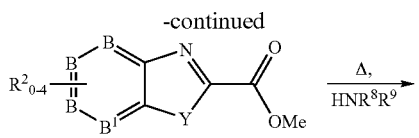

-continued

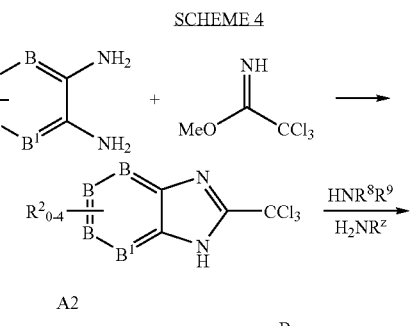

Referring to Scheme 3, there are disclosed the following notes and additions. The starting materials and $HNR^8R^9$ are commercially available or their synthesis is within the skill of the art.

SCHEME 4

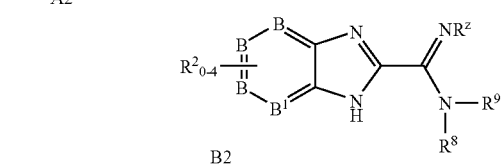

Referring to Scheme 4, there are disclosed the following notes and additions. The starting materials are condensed to form benzimidazole A2. The chorine atoms on benzimidazole A2 are replaced by condensation with a secondary amine with concomitant aminolysis with a primary amine to form the compound B2. For goods yields of compound B2, the secondary amine should be added before the primary amine.

The expression of the $H_4$ receptor in immune cells, including some leukocytes and mast cells, establishes it as an important target for therapeutic intervention in a range of immunological and inflammatory disorders (such as allergic, chronic, or acute inflammation). Specifically $H_4$ receptor ligands are expected to be useful for the treatment or prevention of various mammalian disease states.

Thus, according to the invention, the disclosed compounds, where antagonists of the $H_4$ receptor, and compositions are useful for the amelioration of symptoms associated with, the treatment of, and the prevention of, the following conditions and diseases: inflammatory disorders, asthma, psoriasis, rheumatoid arthritis, ulcerative colitis, Crohn's disease, inflammatory bowel disease, multiple sclerosis, allergic disorders, allergic rhinitis, dermatological disorders, autoimmune disease, lymphatic disorders, atherosclerosis, and immunodeficiency disorders. The disclosed compounds may also be useful as adjuvants in chemotherapy or in the treatment of itchy skin.

Aspects of the invention include (a) a pharmaceutical composition comprising a compound of formula (I), or one or more preferred compounds as described herein, and a pharmaceutically acceptable carrier; (b) a packaged drug comprising (1) a pharmaceutical composition comprising a compound of formula (I) and a pharmaceutically acceptable carrier, and (2) instructions for the administration of said composition for the treatment or prevention of an $H_4$-mediated disease or condition.

The invention also provides a method for treating an $H_4$-mediated condition in a patient, said method comprising administering to the patient a pharmaceutically effective amount of a composition comprising a compound of formula (I) and other disclosed or preferred compounds. For example, the invention features a method for treating an $H_4$ mediated condition in a patient, said method comprising administering to the patient a pharmaceutically effective $H_4$-antagonizing amount of a composition comprising a compound of formula (I).

The effect of an antagonist may also be produced by an inverse agonist. Inverse agonism describes the property of a compound to actively turn off a receptor that displays constitutive activity. Constitutive activity can be identified in cells that have been forced to over-express the human $H_4$ receptor. Constitutive activity can be measured by examining cAMP levels or by measuring a reporter gene sensitive to cAMP levels after a treatment with a cAMP-stimulating agent such as forskolin. Cells that over-express $H_4$ receptors will display lower cAMP levels after forskolin treatment than non-expressing cells. Compounds that behave as $H_4$ agonists will dose-dependently lower forskolin-stimulated cAMP levels in $H_4$-expressing cells. Compounds that behave as inverse $H_4$ agonists will dose-dependently stimulate cAMP levels in $H_4$-expressing cells. Compounds that behave as $H_4$ antagonists will block either $H_4$ agonist-induced inhibition of cAMP or inverse $H_4$ agonist-induced increases in cAMP.

Further embodiments of the invention include disclosed compounds that are inhibitors of a mammalian histamine $H_4$ receptor function, inhibitors of inflammation or inflammatory responses in vivo or in vitro, modulators of the expression of a mammalian histamine $H_4$ receptor protein, inhibitors of polymorphonuclear leukocyte activation in vivo or in vitro, or combinations of the above, and corresponding methods of treatment, prophylaxis, and diagnosis comprising the use of a disclosed compound.

Those skilled in the art will be able to determine, according to known methods, the appropriate dosage for a patient, taking into account factors such as age, weight, general health, the type of symptoms requiring treatment, and the presence of other medications. In general, an effective amount will be between 0.01 and 1000 mg/kg per day, preferably between 0.5 and 300 mg/kg body weight, and daily dosages will be between 10 and 5000 mg for an adult subject of normal weight. Capsules, tablets or other formulations (such as liquids and film-coated tablets) may be of between 0.5 and 200 mg, such as 1, 3, 5, 10, 15, 25, 35, 50 mg, 60 mg, and 100 mg and can be administered according to the disclosed methods.

Dosage unit forms include tablets, capsules, pills, powders, granules, aqueous and nonaqueous oral solutions and suspensions, and parenteral solutions packaged in containers adapted for subdivision into individual doses. Dosage unit forms can also be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

EXAMPLES

General Experimental:

NMR spectra were obtained on either a Bruker model DPX400 (400 MHz) or DPX500 (500 MHz) spectrometer. The format of the $^1H$ NMR data below is: chemical shift in ppm down field of the tetramethylsilane reference (multiplicity, coupling constant J in Hz, integration).

Mass spectra were obtained on an Agilent series 1100 MSD using electrospray ionization (ESI) in either positive or negative mode as indicated. The "mass calculated" for a molecular formula is the monoisotopic mass of the compound.

Reversed-Phase HPLC

Reversed-phase HPLC retention times are reported in minutes, using the method described below.

| Instrument: | Gilson 215 |
|---|---|
| Mobile Phase: | Acetonitrile (0.05% Trifluoroacetic Acid, TFA)/Water (0.05% TFA) |
| Flow rate: | 25 mL/min |
| Gradient: | |
| 1) 0.0 min | 2% Acetonitrile, 0.05% TFA |
| 2) 18.0 min | 98% Acetonitrile, 0.05% TFA |
| Column: | YMC ODS-A (5 µm, 30 × 150 mm) |
| Temperature: | 25° C. |
| Wavelength: | Dual detection at 254 and 220 nM. |

Normal-Phase Silica Gel Column Chromatography

Normal-phase column chromatography was accomplished using ISCO Foxy 200 or ISCO OPTIX 10X systems employ-

Example 1

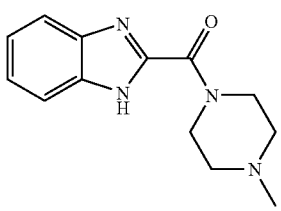

(1H-Benzoimidazol-2-yl)-(4-methyl-piperazin-1-yl)-methanone

General Procedure 1:

A. 2-Trichloromethyl-1H-benzoimidazole. Methyl 2,2,2-trichloroacetimidate (1.63 mL, 9.22 mmol) was added to a solution of phenylenediamine (1.0 g, 9.2 mmol) in acetic acid (30 mL), which was then stirred at room temperature for 1 h. Water (20 mL) was added to the mixture, and the resultant precipitate was collected. The solid was washed with water (2×30 mL) and dried under vacuum to afford 1.90 g (88%) of 2-trichloromethyl-1H-benzoimidazole, which was used without further purification. MS (ESI): mass calculated for $C_8H_5Cl_3N_2$, 233.95; m/z found, 235.0 [M+H]$^+$. $^1$HNMR (400 MHz, CDCl$_3$): 13.45 (br s, 1H), 7.73-7.65 (m, 2H), 7.39-7.30 (m, 2H).

General Procedure 2:

B. (1H-Benzoimidazol-2-yl)-(4-methyl-piperazin-1-yl)-methanone. To a suspension of 2-trichloromethyl-1H-benzoimidazole (100 mg, 0.42 mmol) in 3:1 acetonitrile/water (4.0 mL) was added N-methylpiperazine (0.93 mL, 0.84 mmol) followed by 4 M K$_2$CO$_3$ (0.30 mL). The reaction mixture was stirred for 24 h and was then diluted with satd aq NaHCO$_3$ (3 mL) and extracted with dichloromethane (3×5 mL). The combined extracts were dried (Na$_2$SO$_4$) and then concentrated under reduced pressure. The crude product was purified on silica gel (10 g; 4% methanol/dichloromethane) to afford 54 mg (52%) of the title compound. MS (ESI): mass calculated for $C_{13}H_{16}N_4O$, 244.13; m/z found, 245.2 [M+H]$^+$. $^1$H NMR (400 MHz, DMSO-d$_6$): 13.2 (s, 1H), 7.74 (d, J=7.3 Hz, 2H), 7.53 (d, J=8.3 Hz, 2H), 7.34-7.24 (m, 2H), 4.454.42 μm, 2H), 3.71 (t, J=5.2 Hz, 2H), 2.42-2.40 (m, 4H), 2.22 (s, 3H). $^{13}$C NMR (400 MHz, DMSO-d$_6$): 158.1, 145.5, 142.3, 133.2, 124.1, 122.4, 120.1, 112.2, 55.0, 54.4, 46.0, 45.5, 42.3.

Alternative Preparation of Example 1 (Scheme 1)

A. Benzimidazole-2-carboxylic Acid. 2-Hydroxymethyl-benzimidazole (6.75 mmol) was added to a flask containing hot water (25 mL). A 2 N Na$_2$CO$_3$ solution (5 mL) was added to the reaction mixture until it reached pH 10-12, followed by addition of KMnO$_4$ (~10 mmol). The reaction mixture was then allowed to reflux for 0.5 h. The hot solution was filtered, and the filtrate was cooled to room temperature and 3 N acetic acid was added until the pH reached 3-4. The resulting white precipitate was collected by filtration and rinsed with water and ether to obtain the title intermediate. MS (ESI): mass calculated for $C_8H_6N_2O_2$, 162.04; m/z found, 163.10 [M+H]$^+$. $^1$H NMR (400 MHz, CD$_3$OD): 7.61-7.55 (m, 2H), 7.44-7.38 (m, 2H).

B. (1H-Benzoimidazol-2-yl)-(4-methyl-piperazin-1-yl)-methanone. Diisopropylethylamine (2.2 mmol) was added to a solution of benzimidazole-2-carboxylic acid (3.59 mmol), O-(7-azabenzotriazol-1-yl)-N,N,N',N'-tetramethyluronium hexafluorophosphate (HATU, 3.00 mmol), 1-hydroxy-7-aza-benzotriazole (HOAT, 3.00 mmol), and 1-methylpiperazine (2.00 mmol) in DMF (0.5 M). The reaction mixture was allowed to stir at room temperature overnight. The solvent was removed, and the residue was dissolved in EtOAc. The solution was washed with 1 N HCl, satd aq NaHCO$_3$ and brine. It was then dried (Na$_2$SO$_4$), filtered, and concentrated to obtain the crude product as a viscous oil, which was purified on silica gel (40 g; 3-10% methanol (2 M NH$_3$)/dichloromethane), yielding the title compound (1.68 mmol, 47%). Elemental analysis: calculated for $C_{13}H_{16}N_4O$, C, 63.91; H, 6.60; N, 22.93. Found C, 63.76; H, 6.79; N, 22.87. The MS and $^1$H NMR data matched that of the sample prepared above.

Example 2

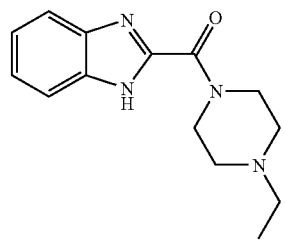

(1H-Benzoimidazol-2-yl)-(4-ethyl-piperazin-1-yl)-methanone

The reaction was carried out as described in General Procedure 2 using 2-trichloromethyl-1H-benzoimidazole (Example 1, 100 mg, 0.42 mmol) and N-ethylpiperazine (0.10 mL, 0.84 mmol). Purification afforded 16 mg (15%) of the title compound. MS (ESI): mass calculated for $Cl_{14}H_{18}N_4O$, 258.15; m/z found, 259.2 [M+H]$^+$. $^1$H NMR (400 MHz, CDCl$_3$): 11.60 (br s, 1H), 7.82 (d, J=8.0 Hz, 1H), 7.54 (d, J=8.0 Hz, 1H), 7.35-7.30 (m, 2H), 4.82-4.80 (m, 2H), 3.97-3.95 (m, 2H), 2.63-2.59 (m, 4H), 2.48 (q, J=7.2 Hz, 2H), 1.14 (t, J=7.2 Hz, 3H).

Example 3

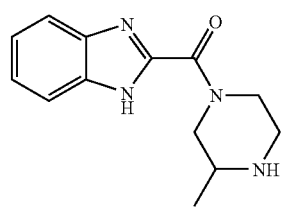

(1H-Benzoimidazol-2-yl)-(3-methyl-piperazin-1-yl)-methanone

The reaction was carried out as described in General Procedure 2 using 2-trichloromethyl-1H-benzoimidazole (Example 1, 100 mg, 0.42 mmol) and 2-methylpiperazine (84 mg, 0.84 mmol). Purification afforded 55 mg (54%) of the title compound. MS (ESI): mass calculated for $C_{13}H_{16}N_4O$, 244.13; m/z found, 245.2 $[M+H]^+$. $^1H$ NMR (400 MHz, $CDCl_3$) a mixture of rotamers: 12.1 (br s, 1H), 7.80-7.52 (m, 2H), 7.33-7.31 (m, 2H), 6.02 (d, J=12.9 Hz, 0.5H), 5.93 (d, J=12.9 Hz, 0.5H), 4.78-4.73 (m, 1H), 3.44-3.37 (m, 0.5H), 3.21-2.88 (m, 4H), 2.67-2.62 (m, 0.5H), 1.18 (t, J=6.8 Hz, 3H).

Example 4

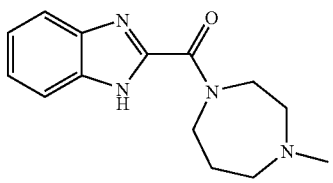

(1H-Benzoimidazol-2-yl)-(4-methyl-[1,4]diazepan-1-yl)-methanone

The reaction was carried out as described in General Procedure 2 using 2-trichloromethyl-1H-benzoimidazole (Example 1, 100 mg, 0.42 mmol) and N-methylhomopiperazine (96 mg, 0.84 mmol). Purification afforded 25 mg (23%) of the title compound. MS (ESI): mass calculated for $C_{14}H_{18}N_4O$, 258.15; m/z found, 259.2 $[M+H]^+$. $^1H$ NMR (400 MHz, $CDCl_3$): 7.66-7.64 (m, 2H), 7.32-7.30 (m, 2H), 4.72-4.69 (m, 1H), 4.63 (t, J=6.3 Hz, 1H), 3.99-3.97 (m, 1H), 3.94 (t, J=6.3 Hz, 1H), 2.90-2.87 (m, 1H), 2.83-2.81 (m, 1H), 2.67-2.63 (m, 2H), 2.41 (d, J=3.5 Hz, 3H), 2.13-2.10 (m, 2H).

Example 5

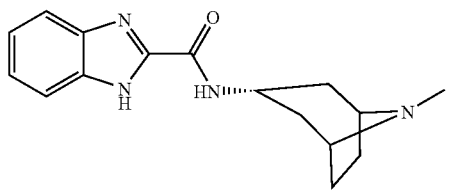

1H-Benzoimidazole-2-carboxylic acid (8-methyl-8-aza-bicyclo[3.2.1]oct-3-yl)-amide The reaction was carried out as described in General Procedure 2 using 2-trichloromethyl-1H-benzoimidazole (Example 1, 100 mg, 0.42 mmol) and 8-methyl-8-azabicyclo[3.2.1]oct-3-ylamine dihydrochloride (172 mg, 0.84 mmol) in tetrahydrofuran (THF, 3 mL). Purification afforded 10 mg (10%) of the title compound. MS (ESI): mass calculated for $C_{16}H_{20}N_4O$, 284.16; m/z found, 285.2 $[M+H]^+$. $^1H$ NMR (400 MHz, $CDCl_3$): 11.70 (br s, 1H), 8.10 (d, J=8.0 Hz, 1H), 7.76 (br s, 1H), 7.43 (br s, 1H), 7.35-7.33 (m, 2H), 4.37 (q, J=7.1 Hz, 1H), 3.25-3.23 (m, 2H), 2.49 (s, 3H), 2.39-2.33 (m, 2H), 2.23 (s, 3H), 2.23-2.18 (m, 2H), 2.02-1.96 (m, 2H), 1.97 (d, J=14.4 Hz, 2H).

Example 6

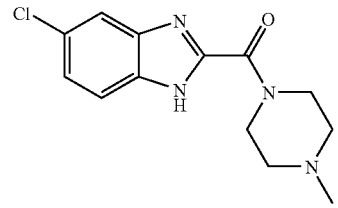

(5-Chloro-1H-benzoimidazol-2-yl)-(4-methyl-piperazin-1-yl)-methanone

The reaction was carried out as described in General Procedure 2 with commercially available 5-chloro-2-trichloromethyl-1H-benzoimidazole (100 mg, 0.37 mmol) and N-methylpiperazine (0.08 mL, 0.75 mmol). Purification afforded 65 mg (63%) of the title compound. MS (ESI): mass calculated for $C_{13}H_{15}ClN_4O$, 278.09; m/z found, 279.2 $[M+H]^+$. $^1H$ NMR (400 MHz, DMSO-$d_6$): 13.29 (s, 1H), 7.67 (br s, 2H), 7.33 (d, J=8.6 Hz, 2H), 4.51-4.48 (m, 2H), 3.71 (t, J=4.6 Hz, 2H), 2.41-2.39 (m, 4H), 2.22 (s, 3H).

Alternative Preparation of Example 6 (Scheme 1)

A. (5-Chloro-1H-benzoimidazol-2-yl)-methanol. A mixture of 3-chloro-benzene-1,2-diamine (5.68 g) in 4 N HCl (40 mL) was treated with glycolic acid (7 mL, 70% solution in water) and refluxed for 2 h. The mixture was cooled and filtered. The filtrate was then neutralized with concentrated $NH_4OH$, and the resulting solids were collected by filtration and dried under vacuum to give the title intermediate (6.59 g). This material was used in Step B without further purification.

B. 5-Chloro-1H-benzoimidazole-2-carboxylic acid. A mixture of (5-Chloro-1H-benzoimidazol-2-yl)-methanol (3.8 g) suspended in 2 N sodium carbonate (110 mL) was treated with a solution of $KMnO_4$ (4.935 g in 310 mL of water). The resulting mixture was heated to 100° C. for 2 h and then filtered. The filtrate was cooled to room temperature, and the solution was adjusted to acidic pH, via addition of 3 N acetic acid, to afford a precipitate. The solid material was isolated by filtration, washed with water and dried under vacuum to give the title intermediate (2.910 g). This material was used in Step C without further purification.

C. (5-Chloro-1H-benzoimidazol-2-yl)-(4-methyl-piperazin-1-yl)-methanone. 5-chloro-1H-benzoimidazole-2-carboxylic acid (0.197 g) in DMF (3 mL) was treated with 1,1'-carbonyldiimidazole (CDI; 0.163 g) at room temperature, and the mixture was stirred for 1 h. The resulting mixture was treated with N-methylpiperazine (0.111 mL) and was stirred at room temperature for 16 h. This mixture was then diluted with water (50 mL) and extracted with dichloromethane (3×20 mL). The combined extracts were washed with brine, dried ($Na_2SO_4$), and then concentrated under reduced pressure. The residue was purified on silica gel (10 g; 0-5% methanol (2 M $NH_3$)/dichloromethane) to give the title compound as a white solid (0.160 g). The MS and $^1H$ NMR data matched that of the compound prepared above.

Example 7

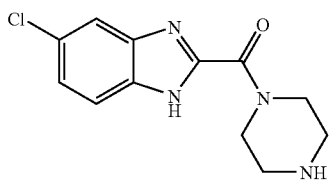

(5-Chloro-1H-benzoimidazol-2-yl)-piperazin-1-yl-methanone

The reaction was carried out as described in General Procedure 2 with commercially available 5-chloro-2-trichloromethyl-1H-benzoimidazole (100 mg, 0.37 mmol) and piperazine (64 mg, 0.75 mmol) in THF (3 mL). Purification afforded 10 mg (10%) of the title compound. MS (ESI): mass calculated for $C_{12}H_{13}ClN_4O$, 264.08; m/z found, 265.2 [M+H]$^+$. $^1$H NMR (400 MHz, DMSO-d$_6$): 13.29 (s, 1H), 7.67 (br s, 2H), 7.33 (d, J=8.6 Hz, 2H), 4.50-4.47 (m, 2H), 3.71 (t, J=4.6 Hz, 2H), 2.41-2.39 (m, 4H), 2.22 (s, 3H).

Example 8

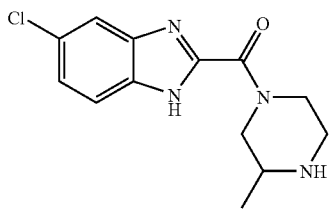

(5-Chloro-1H-benzoimidazol-2-yl)-(3-methyl-piperazin-1-yl)-methanone

The reaction was carried out as described in General Procedure 2 using commercially available 5-chloro-2-trichloromethyl-1H-benzoimidazole (100 mg, 0.37 mmol) and 2-methylpiperazine (74 mg, 0.74 mmol). Purification afforded 41 mg (40%) of the title compound. MS (ESI): mass calculated for $C_{13}H_{15}ClN_4O$, 278.09; m/z found, 279.2 [M+H]$^+$. $^1$H NMR (400 MHz, CDCl$_3$) a mixture of rotamers: 7.61-7.52 (b m, 2H), 7.27 (d, J=8.8 Hz, 2H), 6.00 (d, J=12.6 Hz, 0.5H), 5.89 (d, J=12.6 Hz, 0.5H), 4.75-4.71 (m, 1H), 3.19-3.16 (m, 0.5H), 3.21-2.88 (m, 4H), 2.68-2.65 (m, 0.5H), 1.21-1.17 (m, 3H).

Example 9

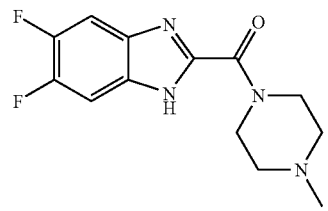

(5,6-Difluoro-1H-benzoimidazol-2-yl)-(4-methyl-piperazin-1-yl)-methanone

A. 5,6-Difluoro-2-trichloromethyl-1H-benzoimidazole. The reaction was carried out as described in General Procedure 1 with 4,5-difluoro-1,2-phenylenediamine (1.00 g, 6.94 mmol). The dried precipitate was triturated with dichloromethane (3×10 mL) followed by hexanes (3×10 mL) to give 890 mg (48%) of the title intermediate. MS (ESI): mass calculated for $C_8H_3Cl_3F_2N_2$, 269.93; m/z found, 271.0 [M+H]$^+$. $^1$H NMR (400 MHz, CDCl$_3$): 10.0 (s, 1H), 7.65 (dd, J=10.0, 7.3, 1H), 7.32 (dd, J=9.8, 6.3, 1H).

B. (5,6-Difluoro-1H-benzoimidazol-2-yl)-(4-m th 1-piperazin-1yl)-methanone. The reaction was carried out as described in General Procedure 2 with 5,6-difluoro-2-trichloromethyl-1H-benzoimidazole (100 mg, 0.37 mmol) and N-methylpiperazine (0.08 mL, 0.75 mmol). Purification afforded 42 mg (40%) of the title compound. MS (ESI): mass calculated for $C_{13}H_{14}F_2N_4O$, 280.11; m/z found, 281.2 [M+H]$^+$. $^1$H NMR (400 MHz, CDCl$_3$): 11.9 (br s, 1H), 7.56-7.31 (bm, 2H), 4.78-4.75 (m, 2H), 3.95 (t, J=5.1 Hz, 2H), 2.58 (t, J=5.1 Hz, 4H), 2.37 (s, 3H).

Example 10

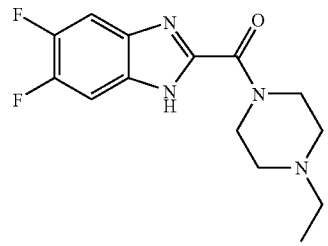

(5,6-Difluoro-1H-benzoimidazol-2-yl)-(4-ethyl-piperazin-1-yl)-methanone

The reaction was carried out as described in General Procedure 2 using 5,6-difluoro-2-trichloromethyl-1H-benzoimidazole (Example 9, Step A, 100 mg, 0.39 mmol) and N-ethylpiperazine (0.10 mL, 0.79 mmol). Purification afforded 31 mg (28%) of the title compound. MS (ESI): mass calculated for $C_{14}H_{16}F_2N_4O$, 294.13; m/z found, 295.2 [M+H]$^+$. $^1$H NMR (400 MHz, CDCl$_3$): 11.70 (br s, 1H), 7.61 (br s, 1H), 7.31 (br s, 1H), 4.78-4.76 (m, 2H), 3.96-3.92 (m, 2H), 2.64-2.62 (m, 4H), 2.49 (q, J=7.2 Hz, 2H), 1.15 (t, J=7.2 Hz, 3H).

Example 11

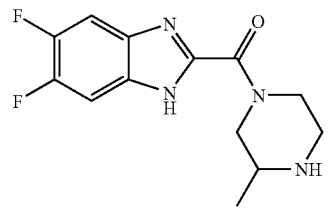

(5,6-Difluoro-1H-benzoimidazol-2-yl)-(3-methyl-piperazin-1-yl)-methanone

The reaction was carried out as described in General Procedure 2 using 5,6-difluoro-2-trichloromethyl-1H-benzoimidazole (Example 9, Step A, 100 mg, 0.37 mmol) and 2-methylpiperazine (74 mg, 0.37 mmol). Purification afforded 30 mg (28%) of the title compound. MS (ESI): mass calculated for $C_{13}H_{14}F_2N_4O$, 280.11; m/z found, 281.2 [M+H]$^+$. $^1$H NMR (400 MHz, CDCl$_3$) a mixture of rotamers: 11.6 (br s, 1H), 7.35-7.27 (bm, 2H), 5.99 (d, J=12.6 Hz, 0.5H), 5.88 (d, J=12.6 Hz, 0.5H), 4.69-4.66 (m, 1H), 3.19-3.16 (m, 0.5H), 3.04-2.67 (m, 4H), 2.67-2.63 (m, 0.5H), 1.20-1.18 (m, 3H).

Example 12

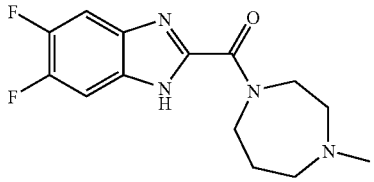

(5,6-Difluoro-1H-benzoimidazol-2-yl)-(4-methyl-[1,4]diazepan-1-yl)-methanone

The reaction was carried out as described in General Procedure 2 using 5,6-difluoro-2-trichloromethyl-1H-benzoimidazole (Example 9, Step A, 100 mg, 0.37 mmol), and N-methylhomopiperazine (84 mg, 0.74 mmol). Purification afforded 29 mg (27%) of the title compound. MS (ESI): mass calculated for $C_{14}H_{16}F_2N_4O$, 294.13; m/z found, 295.2 [M+H]$^+$. $^1$H NMR (400 MHz, CDCl$_3$):

11.12 (br s, 1H), 7.47-7.40 (bm, 2H), 3.92-3.89 (m, 1H), 3.87 (t, J=6.0 Hz, 1H), 3.99-3.97 (m, 1H), 3.94 (t, J=6.3 Hz, 1H), 2.90-2.87 (m, 1H), 2.83-2.81 (m, 1H), 2.67-2.63 (m, 2H), 2.41 (d, J=3.5 Hz, 3H), 2.13-2.10 (m, 2H).

Example 13

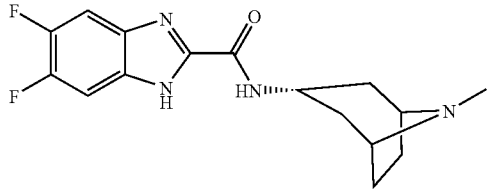

5,6-Difluoro-1H-benzoimidazole-2-carboxylic acid (8-methyl-8-aza-bicyclo[3.2.1]oct-3-yl)-amide The reaction was carried out as described in General Procedure 2 using 5,6-difluoro-2-trichloromethyl-1H-benzoimidazole (Example 9, Step A, 100 mg, 0.37 mmol) and 8-methyl-8-aza-bicyclo[3.2.1]oct-3-ylamine dihydrochloride (157 mg, 0.74 mmol). Purification afforded 25 mg (21%) of the title compound. MS (ESI): mass calculated for $C_{16}H_{18}F_2N_4O$, 320.14; m/z found, 321.2 [M+H]$^+$. $^1$H NMR (400 MHz, CDCl$_3$): 8.04 (d, J=8 Hz, 1H), 7.41 (br s, 2H), 4.37-4.32 (m, 1H), 3.25 (s, 2H), 2.40-2.34 (m, 5H), 2.26-2.22 (m, 2H), 1.97-1.95 (m, 2H), 1.88-1.85 (d, J=12.0 Hz, 2H).

Example 14

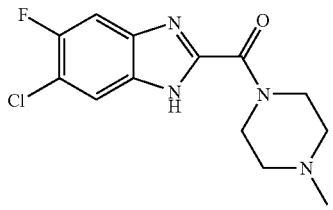

(6-Chloro-5-fluoro-1H-benzoimidazol-2-yl)-(4-methyl-piperazin-1-yl)-methanone

A. 6-Chloro-5-fluoro-2-trichloromethyl-1H-benzoimidazole. The reaction was carried out as described in General Procedure 1 with 4-fluoro-5-chloro-1,2-phenylenediamine (1.00 g, 6.25 mmol). The dried precipitate was triturated with dichloromethane (3×10 mL) followed by hexanes (3×10 mL) to give 1.09 g (59%) of 6-chloro-5-fluoro-2-trichloromethyl-1H-benzoimidazole. MS (ESI): mass calculated for $C_8H_3Cl_4FN_2$, 285.90; m/z found, 287.1 [M+H]$^+$. $^1$H NMR (400 MHz, CDCl$_3$): 10.2 (br s, 1H), 7.57 (d, J=5.6, 1H), 7.31 (d, J=9.0, 1H).

B. (6-Chloro-5-fluoro-1H-benzoimidazol-2-yl)-(4-methyl-piperazin-1-yl)-methanone. The reaction was carried out as described in General Procedure 2 with 6-chloro-5-fluoro-2-trichloromethyl-1H-benzoimidazole (100 mg, 0.35 mmol) and N-methylpiperazine (0.08 mL, 0.70 mmol). Purification afforded 58 mg (56%) of the title compound. MS (ESI): mass calculated for $C_{13}H_{14}ClFN_4O$, 296.08; m/z found, 297.2 [M+H]$^+$. $^1$H NMR (400 MHz, CDCl$_3$): 7.71-7.69 (br s, 1H), 7.39-7.37 (br s, 2H), 4.65-4.63 (m, 2H), 3.87 (t, J=4.5 Hz, 2H), 2.59-2.57 (m, 4H), 2.37 (s, 3H).

Example 15

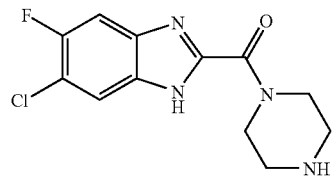

(6-Chloro-5-fluoro-1H-benzoimidazol-2-yl)-piperazin-1-yl-methanone

The reaction was carried out as described in General Procedure 2 using 6-chloro-5-fluoro-trichloromethyl-1H-benzoimidazole (Example 14, Step A, 100 mg, 0.35 mmol) and piperazine (59 mg, 0.70 mmol). Purification afforded 10 mg (10%) of the title compound. MS (ESI): mass calculated for $C_{12}H_{12}ClFN_4O$, 282.07; m/z found, 283.1 [M+H]$^+$. $^1$H NMR (400 MHz, CDCl$_3$): 7.77-7.67 (m, 2H), 7.46-7.37 (m, 2H), 4.72-4.68 (m, 2H), 3.91-3.85 (m, 2H), 3.07-3.02 (m, 4H).

Example 16

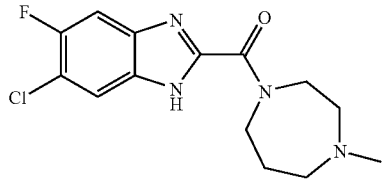

(6-Chloro-5-fluoro-1H-benzoimidazol-2-yl)-(4-methyl-[1,4]diazepan-1-yl)-methanone The reaction was carried out as described in General Procedure 2 using 6-chloro-5-fluoro-2-trichloromethyl-1H-benzoimidazole (Example 14, Step A, 100 mg, 0.35 mmol) and N-methylhomopiperazine (79 mg, 0.70 mmol). Purification afforded 29 mg (27%) of the title compound. MS (ESI): mass calculated for $C_{14}H_{16}ClFN_4O$, 310.10; m/z found, 311.2 [M+H]$^+$. $^1$H NMR (400 MHz, CDCl$_3$): 11.2 (br s, 1H), 7.72

(br s, 1H), 7.41 (br s, 1H), 4.64-4.61 (m, 1H), 3.88 (t, J=6.1 Hz, 1H), 3.93-3.91 (m, 1H), 3.88 (t, J=6.1 Hz, 1H), 2.87-2.84 (m, 1H), 2.80-2.78 (m, 1H), 2.66-2.62 (m, 2H), 2.41 (d, J=5.1 Hz, 3H), 2.17-2.11 (m, 2H).

Example 17

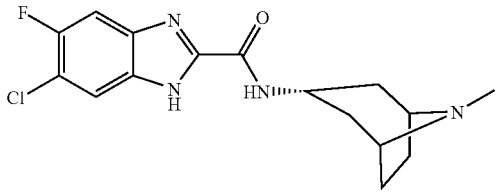

6-Chloro-5-fluoro-1H-benzoimidazole-2-carboxylic acid (8-methyl-8-aza-bicyclo[3.2.1]oct-3-yl)-amide The reaction was carried out as described in General Procedure 2 with 6-chloro-5-fluoro-2-trichloromethyl-1H-benzoimidazole (Example 14, Step A, 100 mg, 0.35 mmol) and 8-methyl-8-aza-bicyclo[3.2.1]oct-3-ylamine dihydrochloride (149 mg, 0.70 mmol). Purification afforded 35 mg (30%) of the title compound. MS (ESI): mass calculated for $C_{16}H_{18}ClFN_4O$, 336.12; m/z found, 337.2 [M+H]+. 1H NMR (400 MHz, CDCl3): 8.01 (d, J=8 Hz, 1H), 7.71 (br s, 1H), 7.52-7.38 (m, 1H), 4.37-4.31 (m, 1H), 3.24 (s, 2H), 2.39-2.32 (m, 5H), 2.26-2.22 (m, 2H), 1.96-1.95 (m, 2H), 1.86 (d, J=12.0 Hz, 2H).

Example 18

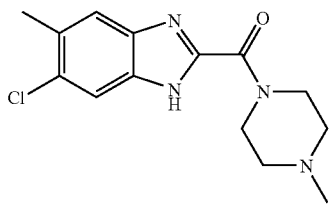

(5-Chloro-6-methyl-1H-benzoimidazol-2-yl)-(4-methyl-piperazin-1-yl)-methanone

A. 5-Chloro-6-methyl-2-trichloromethyl-1H-benzoimidazole. The reaction was carried out as described in General Procedure 1 with 5-chloro-6-methyl-1,2-phenylenediamine (1.00 g, 6.41 mmol). The dried precipitate was triturated with dichloromethane (3×10 mL) followed by hexanes (3×10 mL) to give 950 mg (53%) of the title intermediate. MS (ESI): mass calculated for $C_9H_6Cl_4N_2$, 281.93; m/z found, 283.0 [M+H]+. 1H NMR (400 MHz, CDCl3): 7.70 (s, 1H), 7.52 (s, 1H).

B. (5-Chloro-6-methyl-1H-benzoimidazol-2-yl)-(4-methyl-piperazin-1-yl)-methanone. The reaction was carried out as described in General Procedure 2 with 5-chloro-6-methyl-2-trichloromethyl-1H-benzoimidazole (100 mg, 0.35 mmol) and N-methylpiperazine (0.08 mL, 0.71 mmol). Purification afforded 36 mg (35%) of the title compound. MS (ESI): mass calculated for $C_{14}H_{17}ClN_4O$, 292.11; m/z found, 293.2 [M+H]+. 1H NMR (400 MHz, CDCl3): 11.5 (br s, 1H), 7.71-7.32 (bm, 2H), 4.74-4.72 (m, 2H), 3.97-3.94 (m, 2H), 2.58 (t, J=5.1 Hz, 4H), 2.48 (s, 3H), 2.38 (s, 3H).

Example 19

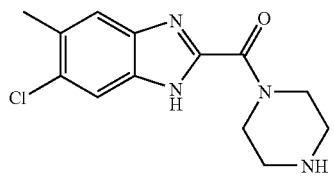

(5-Chloro-6-methyl-1H-benzoimidazol-2-yl)-piperazin-1-yl-methanone

The reaction was carried out as described in General Procedure 2 using 5-chloro-6-methyl-trichloromethyl-1H-benzoimidazole (Example 18, Step A, 100 mg, 0.35 mmol) and piperazine (60 mg, 0.71 mmol). Purification afforded 8 mg (8%) of the title compound. MS (ESI): mass calculated for $C_{13}H_{15}ClN_4O$, 278.09; m/z found, 279.1 [M+H]+. 1H NMR (400 MHz, CDCl3): 7.75-7.28 (m, 2H), 4.72-4.69 (m, 2H), 3.85-3.82 (m, 2H), 3.03-3.00 (m, 4H), 2.49 (s, 3H).

Example 20

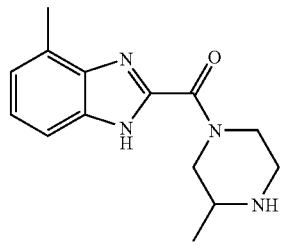

(4-Methyl-1H-benzoimidazol-2-yl)-(3-methyl-piperazin-1-yl)-methanone

A. 4-Methyl-2-trichloromethyl-1H-benzoimidazole. The reaction was carried out as described in General Procedure 1 using 2,3-diaminotoluene (1.19 g, 9.74 mmol) and methyl-2,2,2-trichloroacidimidate (1.20 mL, 9.74 mmol). Purification on silica gel (40 g; 40% EtOAc/hexanes) afforded 830 mg (34%) of the title intermediate. MS (ESI): mass calculated for $C_9H_7Cl_3N_2$, 247.97; m/z found, 249.0 [M+H]+. 1H NMR (400 MHz, CDCl3): 9.78 (s, 1H), 7.52 (br s, 1H), 7.27 (d, J=7.4, 8.1 Hz, 1H), 7.17 (d, J=7.4 Hz, 1H), 2.64 (s, 3H).

B. (4-Methyl-1H-benzoimidazol-2-yl)-(3-methyl-piperazin-1-yl)-methanone. The reaction was carried out as described in General Procedure 2 using 4-methyl-2-trichloromethyl-1H-benzoimidazole (100 mg, 0.40 mmol) and 2-methylpiperazine (80 mg, 0.80 mmol) in THF (3 mL). Purification afforded 27 mg (26%) of the title compound. MS (ESI): mass calculated for $C_{14}H_{18}N_4O$, 258.15; m/z found, 259.2 [M+H]+. 1H NMR (400 MHz, CDCl3) a mixture of rotamers: 11.61-11.58 (m, 1H), 7.68-7.57 (m, 0.5H), 7.24-7.18 (m, 1H), 7.10 (d, J=7.1 Hz, 1H), 6.18-5.84 (m, 1H), 4.73-4.67 (m, 1H), 3.40 (ddd, J=3.03, 12.6, 14.15 Hz, 0.5H), 3.18-3.13 (m, 1H), 3.10-2.86 (m, 3.5H), 2.70-2.45 (m, 4H), 1.80 (br s, 1H), 1.17 (d, J=6.32 Hz, 3H).

Example 21

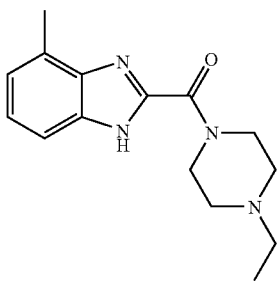

(4-Ethyl-piperazin-1-yl)-(4-methyl-1H-benzoimidazol-2-yl)-methanone

The reaction was carried out as described in General Procedure 2 using 4-methyl-2-trichloromethyl-1H-benzoimidazole (Example 20, Step A, 100 mg, 0.40 mmol) and N-ethylpiperazine (0.10 mL, 0.80 mmol) in THF (3 mL). Purification afforded 67 mg (62%) of the title compound. MS (ESI): mass calculated for $C_{15}H_{20}N_4O$, 272.16; m/z found, 273.2 [M+H]$^+$. $^1$H NMR (400 MHz, CDCl$_3$): 10.89 (s, 1H), 7.64 (d, J=8.6 Hz, 0.5H), 7.33 (d, J=8.6 Hz, 0.5H), 7.22-7.18 (m, 1H), 7.13 (d, J=7.4 Hz, 0.5H), 7.10 (d, J=7.4 Hz, 0.5H), 4.86-4.84 (m, 1H), 4.80-4.78 (m, 1H), 3.93-3.90 (m, 2H), 2.66 (s, 1.5H), 2.63-2.56 (m, 4H), 2.52 (s, 1.5H), 2.48 (q, J=7.3 Hz, 2H), 1.14 (t, J=7.1 Hz, 3H).

Example 22

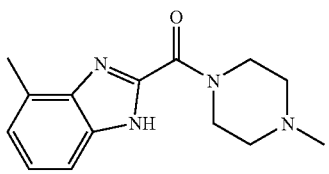

(4-Methyl-1H-benzoimidazol-2-yl)-(4-methyl-piperazin-1-yl)-methanone

The reaction was carried out as described in General Procedure 2 using 4-methyl-2-trichloromethyl-1H-benzoimidazole (Example 20, Step A, 100 mg, 0.40 mmol) and N-methylpiperazine (0.09 mL, 0.80 mmol). Purification afforded 51 mg (50%) of the title compound. MS (ESI): mass calculated for $C_{14}H_{18}N_4O$, 258.15; m/z found, 259.2 [M+H]$^+$. $^1$H NMR (400 MHz, CDCl$_3$): 11.53 (br s, 1H), 7.64 (d, J=8.3 Hz, 0.5H), 7.32 (d, J=8.3 Hz, 0.5H), 7.25-7.18 (m, 1H), 7.10 (t, J=7.3 Hz, 1H), 4.87-4.82 (m, 1H), 4.79-4.75 (m, 1H), 3.95-3.92 (m, 2H), 2.66 (s, 1.5H), 2.59-2.54 (m, 4H), 2.50 (s, 1.5H), 2.36 (s, 3H).

Alternative Preparation of Example 22 (Scheme 1)

A. (4-Methyl-1H-benzoimidazol-2-yl)-methanol. A mixture of 3-methyl-benzene-1,2-diamine (3.77 g, 30.8 mmol) and glycolic acid (5 mL, 70% solution in water) in 4 N HCl (30 mL) was heated to 100° C. for 2 h. The warm mixture was allowed to cool and was filtered. Neutralization of the filtrate with concentrated NH$_4$OH resulted in the formation of a solid, which was collected by filtration, washed with water and dried under vacuum to reveal 0.95 g (19%) of the title intermediate. MS (ESI): mass calculated for $C_9H_{10}N_2O$, 162.08; m/z found, 163.1 [M+H]$^+$. $^1$H NMR (400 MHz, CD$_3$OD): 7.35 (d, J=8.1 Hz, 1H), 7.10 (dd, J=7.3, 8.1 Hz, 1H), 7.00 (d, J=7.3 Hz, 1H), 4.88 (br, 3H), 2.55 (s, 3H).

B. (4-Methyl-1H-benzoimidazol-2-yl)-(4-methyl-piperazin-1-yl)-methanone. To a suspension of (4-methyl-1H-benzoimidazol-2-yl)-methanol (0.84 g, 5.18 mmol) in water (10 mL) was added 2 M Na$_2$CO$_3$ (10 mL). To the mixture was added dropwise a 0.1 M solution of KMnO$_4$ (1.4 g, 8.8 mmol). This mixture was heated to 100° C. for 2 h and was then filtered while hot, and the cooled filtrate was acidified with 3 N acetic acid. The resulting solids were collected by filtration, washed with water and dried under vacuum. The crude acid (0.56 g, 62%) was used in the amide coupling without further purification. To a suspension of the acid (111.6 mg, 0.63 mmol) in DMF (3 mL) was added CDI (108.9 mg, 0.67 mmol), and this mixture was stirred for 1 h. The methyl piperazine was then added (80 µL), and the reaction mixture was stirred 16 h at room temperature. The mixture was poured into water (50 mL) and extracted with dichloromethane. The combined extracts were concentrated under reduced pressure, and the residue was purified on silica gel (10 g; 1-8% methanol (2 M NH$_3$)/dichloromethane) to reveal 124.3 mg (76%) of a white solid. The MS and $^1$H NMR data matched that for the product obtained above.

Example 23

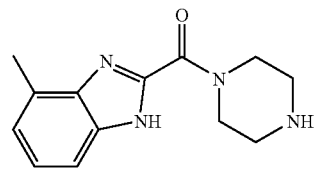

(4-Methyl-1H-benzoimidazol-2-yl)-piperazin-1-yl-methanone

The reaction was carried out as described in General Procedure 2 using 4-methyl-2-trichloromethyl-1H-benzoimidazole (Example 20, Step A, 100 mg, 0.40 mmol) and piperazine (69 mg, 0.80 mmol). Purification afforded 4 mg (4%) of the title compound. MS (ESI): mass calculated for $C_{13}H_{16}N_4O$, 244.13; m/z found, 245.2 [M+H]$^+$. $^1$H NMR (400 MHz, CDCl$_3$): 10.36 (s, 1H), 7.65 (d, J=8.3 Hz, 0.5H), 7.34 (d, J=8.3 Hz, 0.5H), 7.24-7.20 (m, 1H), 7.15 (d, J=7.3 Hz, 0.5H), 7.11 (d, J=7.3 Hz, 0.5H), 4.80-4.78 (m, 1H), 4.75-4.73 (m, 1H), 3.03-2.99 (m, 2H), 2.67 (s, 1.5H), 2.54 (s, 1.5H).

Example 24

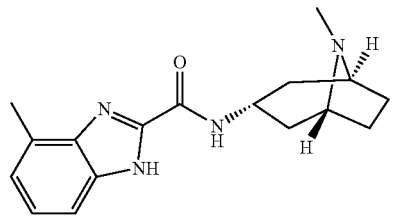

4-Methyl-1H-benzoimidazole-2-carboxylic acid (8-methyl-8-aza-bicyclo[3.2.1]oct-3-yl)-amide The reaction was carried out as described in General Procedure 2 using 4-methyl-2-trichloromethyl-1H-benzoimidazole (Example 20, Step A, 100 mg, 0.40 mmol) and 8-methyl-8-azabicyclo[3.2.1]octan-3-amine dihydrochloride (170 mg, 0.80 mmol). Purification afforded 16 mg (13%) of the title compound. MS (ESI): mass calculated for $C_{17}H_{22}N_4O$, 298.18; m/z found, 299.3 [M+H]$^+$. $^1$H NMR (400 MHz, CDCl$_3$) a mixture of rotamers: 11.65-11.46 (m, 1H), 8.12-8.07 (m, 1H), 7.64 (d, J=8.1 Hz, 0.6H), 7.36 (d, J=8.1 Hz, 0.4H), 7.24 (t, J=8.1 Hz, 1H), 7.14 (d, J=7.3 Hz, 0.6H), 7.11 (d, J=7.3 Hz, 0.4H), 4.34 (quin, J=6.8 Hz, 1H), 3.23 (br s, 2H), 2.68 (s, 1.4H), 2.60 (s, 1.6H), 2.34 (m, 5H), 2.24-2.20 (m, 2H), 2.02-1.96 (m, 2H), 1.87 (d, J=14.4 Hz, 2H).

Example 25

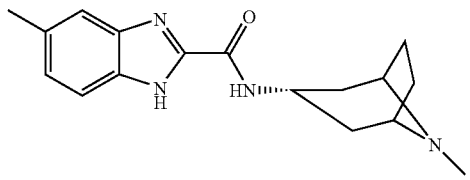

5-Methyl-1H-benzoimidazole-2-carboxylic acid (8-methyl-8-aza-bicyclo[3.2.1]oct-3-yl)-amide A. 5-Methyl-2-trichloromethyl-1H-benzoimidazole. The reaction was carried out as described in General Procedure 1 using 3,4-diaminotoluene (1.33 g, 10.88 mmol) and methyl-2,2,2-trichloroacidimidate (1.33 mL, 10.88 mmol). Purification on silica gel (40 g; 40% EtOAc/hexanes) afforded 980 mg (36%) of the title intermediate. MS (ESI): mass calculated for $C_9H_7Cl_3N_2$, 247.97; m/z found, 249.0 [M+H]$^+$. $^1$H NMR (400 MHz, CDCl$_3$): 9.77 (br s, 1H), 7.60 (br s, 1H), 7.43 (br s, 1H), 7.19 (dd, J=1.3, 8.6 Hz, 1H), 2.50 (s, 3H).

B. 5-Methyl-1H-benzoimidazole-2-carboxylic acid (8-methyl-8-aza-bicyclo[3.2.1]oct-3-yl)-amide. The reaction was carried out as described in General Procedure 2 using 5-methyl-2-trichloromethyl-1H-benzoimidazole (100 mg, 0.40 mmol) and 8-methyl-8-azabicyclo[3.2.1]oct-3-ylamine dihydrochloride (170 mg, 0.80 mmol) in THF (3 mL). Purification afforded 12 mg (10%) of the title compound. MS (ESI): mass calculated for $C_{17}H_{22}N_4O$, 298.18; m/z found, 299.2 [M+H]$^+$. $^1$H NMR (400 MHz, CDCl$_3$): 11.55 (br s, 1H), 8.02-7.96 (m, 1H), 7.67 (d, J=8.4 Hz, 0.55H), 7.58 (br s, 0.45H), 7.42 (d, J=8.6 Hz, 0.45H), 7.33 (br s, 0.55H), 7.18-7.13 (m, 1H), 4.34 (q, J=7.07 Hz, 1H), 3.24-3.22 (m, 2H), 2.49 (s, 3H), 2.39-2.33 (m, 2H), 2.23 (s, 3H), 2.23-2.18 (m, 2H), 2.01-1.95 (m, 2H), 1.88 (d, J=14.4 Hz, 2H).

Example 26

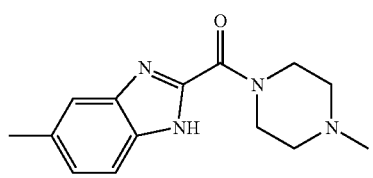

(5-Methyl-1H-benzoimidazol-2-yl)-(4-methyl-piperazin-1-yl)-methanone

The reaction was carried out as described in General Procedure 2 using 5-methyl-2-trichloromethyl-1H-benzoimidazole (Example 25, Step A, 100 mg, 0.40 mmol) and N-methylpiperazine (0.09 mL, 0.80 mmol). Purification afforded 36 mg (35%) of the title compound. MS (ESI): mass calculated for $C_{14}H_{18}N_4O$, 258.15; m/z found, 259.2 [M+H]$^+$. $^1$H NMR (400 MHz, CDCl$_3$): 11.24 (br s, 1H), 7.69 (d, J=8.3 Hz, 0.6H), 7.60 (br s, 0.4H), 7.39 (d, J=8.3 Hz, 0.4H), 7.29 (br s, 0.6H), 7.18 (d, J=8.3 Hz, 0.4H) 7.13 (d, J=8.3 Hz, 0.6H), 4.81-4.77 (m, 2H), 3.95-3.93 (m, 2H), 2.59-2.55 (m, 4H), 2.49 (s, 3H), 2.36 (s, 3H).

Example 27

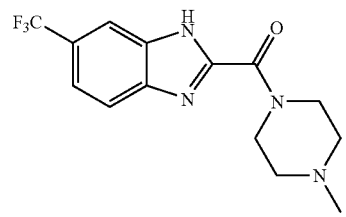

(4-Methyl-piperazin-1-yl)-(5-trifluoromethyl-1H-benzoimidazol-2-yl)-methanone

A. 2-Trichloromethyl-5-trifluoromethyl-1H-benzoimidazole. The reaction was carried out as described in General Procedure 1 using 4-(trifluoromethyl)-1,2-phenylenediamine (1.0 g, 5.68 mmol) and methyl-2,2,2-trichloroacidimidate (0.70 mL, 5.68 mmol). Purification on silica gel (40 g; 40% EtOAc/hexanes) afforded 930 mg (54%) of the title intermediate. MS (ESI): mass calculated for $C_9H_4Cl_3F_3N_2$, 301.94; m/z found, 303.0 [M+H]$^+$. $^1$H NMR (400 MHz, CDCl$_3$): 10.16 (br s, 1H), 8.18 (br s, 0.55H), 7.98 (br d, J=8.08 Hz, 0.5H), 7.83 (br s, 0.45H), 7.71-7.63 (m, 1.5H).

B. (4-Methyl-piperazin-1-yl)-(5-trifluoromethyl-1H-benzoimidazol-2-yl)-methanone. The reaction was carried out as described in General Procedure 2 using 2-trichloromethyl-5-trifluoromethyl-1H-benzoimidazole (100 mg, 0.33 mmol) and N-methylpiperazine (0.07 mL, 0.66 mmol). Purification afforded 42 mg (41%) of the title compound. MS (ESI): mass calculated for $C_{14}H_{15}F_3N_4O$, 312.12; m/z found, 313.2 [M+H]$^+$. $^1$H NMR (400 MHz, CDCl$_3$): 8.01 (br s, 1H), 7.74-7.70 (m, 1H), 7.58 (dd, J=1.3, 8.6 Hz, 1H), 4.78-4.76 (m, 2H), 3.96-3.94 (m, 2H), 2.60-2.56 (m, 4H), 2.37 (s, 3H).

Example 28

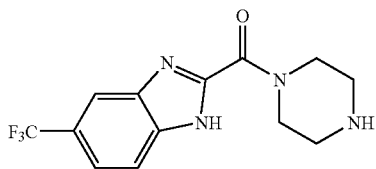

Piperazin-1-yl-(5-trifluoromethyl-1H-benzoimidazol-2-yl)-methanone

The reaction was carried out as described in General Procedure 2 using 2-trichloromethyl-5-trifluoromethyl-1H-benzoimidazole (Example 27, Step A, 100 mg, 0.33 mmol) and piperazine (57 mg, 0.66 mmol). Purification afforded 6 mg (6%) of the title compound. MS (ESI): mass calculated for $C_{13}H_{13}F_3N_4O$, 298.10; m/z found, 299.2 [M+H]+. 1H NMR (400 MHz, CDCl3): 11.01 (br s, 1H), 8.12 (br s, 0.5H), 7.87 (br, 1H), 7.58-7.60 (m, 1.5H), 4.74-4.72 (m, 2H), 3.89-3.86 (m, 2H), 3.06-3.03 (m, 4H).

Example 29

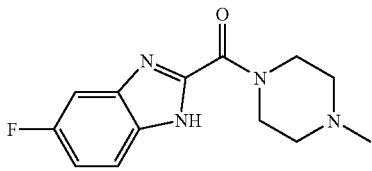

(5-Fluoro-1H-benzoimidazol-2-yl)-(4-methyl-piperazin-1-yl)-methanone

A. 5-Fluoro-2-trichloromethyl-1H-benzoimidazole. The reaction was carried out as described in General Procedure 1 using 4-fluoro-1,2-phenylenediamine (1.0 g, 8.12 mmol) and methyl-2,2,2-trichloroacidimidate (1.0 mL, 8.12 mmol). Trituration of the resulting precipitate afforded 1.20 g (60%) of the title intermediate. MS (ESI): mass calculated for $C_8H_4Cl_3FN_2$, 251.94; m/z found, 253.0 [M+H]+. 1H NMR (400 MHz, CDCl3): 7.64 (br s, 1H), 7.31 (br s, 1H), 7.07 (dt, J=2.27, 9.09 Hz, 1H).

B. (5-Fluoro-1H-benzoimidazol-2-yl)-(4-methyl-piperazin-1-yl)-methanone. The reaction was carried out as described in General Procedure 2 using 5-fluoro-2-trichloromethyl-1H-benzoimidazole (100 mg, 0.39 mmol) and N-methylpiperazine (0.09 mL, 0.79 mmol). Purification afforded 28 mg (27%) of the title compound. MS (ESI): mass calculated for $C_{13}H_{15}FN_4O$, 262.12; m/z found, 236.2 [M+H]+. 1H NMR (400 MHz, CDCl3): 11.55 (br s, 1H), 7.74 (br s, 0.5H), 7.46 (br s, 1H), 7.19-7.17 (m, 0.5H), 7.09-7.07 (m, 1H), 4.79-4.77 (m, 2H), 3.95-3.92 (m, 2H), 2.59-2.57 (m, 4H), 2.37 (s, 3H).

Example 30

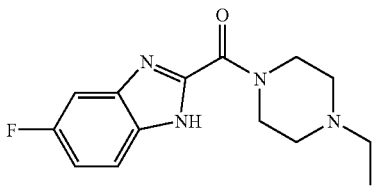

(4-Ethyl-piperazin-1-yl)-(5-fluoro-1H-benzoimidazol-2-yl)-methanone

The reaction was carried out as described in General Procedure 2 using 5-fluoro-2-trichloromethyl-1H-benzoimidazole (Example 29, Step A, 100 mg, 0.39 mmol) and N-ethylpiperazine (0.10 mL, 0.79 mmol). Purification afforded 30 mg (28%) of the title compound. MS (ESI): mass calculated for $C_{14}H_{17}FN_4O$, 276.14; m/z found, 277.2 [M+H]+. 1H NMR (400 MHz, CDCl3): 11.62 (br s, 1H), 7.74 (br s, 0.5H), 7.46 (br s, 1H), 7.19 (br s, 0.5H), 7.08 (br s, 1H), 4.80-4.76 (m, 2H), 3.96-3.93 (m, 2H), 2.63-2.60 (m, 4H), 2.50 (q, J=7.3 Hz, 2H), 1.14 (t, J=7.3 Hz, 3H).

Example 31

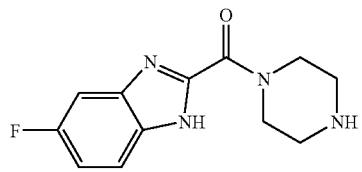

(5-Fluoro-1H-benzoimidazol-2-yl)-piperazin-1-yl-methanone

The reaction was carried out as described in General Procedure 2 using 5-fluoro-2-trichloromethyl-1H-benzoimidazole (Example 29, Step A, 100 mg, 0.39 mmol) and piperazine (68 mg, 0.79 mmol). Purification afforded 7 mg (7%) of the title compound. MS (ESI): mass calculated for $C_{12}H_{13}FN_4O$, 248.11; m/z found, 249.2 [M+H]+. 1H NMR (400 MHz, CDCl3): 11.26 (br s, 1H), 7.72 (br s, 0.5H), 7.46 (br s, 1H), 7.19 (br s, 0.5H), 7.09 (br s, 1H), 4.74-4.71 (m, 2H), 3.89-3.86 (m, 2H), 3.05-3.02 (m, 4H).

Example 32

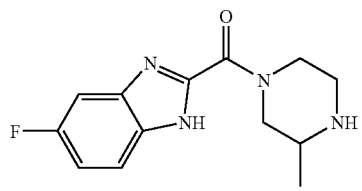

(5-Fluoro-1H-benzoimidazol-2-yl)-(3-methyl-piperazin-1-yl)-methanone

The reaction was carried out as described in General Procedure 2 using 5-fluoro-2-trichloromethyl-1H-benzoimidazole (Example 29, Step A, 100 mg, 0.39 mmol) and 2-methylpiperazine (79 mg, 0.79 mmol). Purification afforded 17 mg (17%) of the title compound. MS (ESI): mass calculated for $C_{13}H_{15}FN_4O$, 262.12; m/z found, 263.2 [M+H]+. 1H NMR (400 MHz, CDCl3): 11.45 (br s, 1H), 7.74 (br s, 0.5H), 7.46 (br s, 1H), 7.19 (br s, 0.5H), 7.08 (br s, 1H), 6.57-6.03 (m, 0.5H), 5.94-5.89 (m, 0.5H), 4.72-4.65 (m, 1H), 3.42-3.35 (m, 0.5H), 3.20-3.14 (m, 1H), 3.08-2.87 (m, 3H), 2.66-2.59 (m, 0.5H), 1.19 (d, J=6.3 Hz, 1.5H), 1.18 (d, J=6.3 Hz, 1.5H).

Example 33

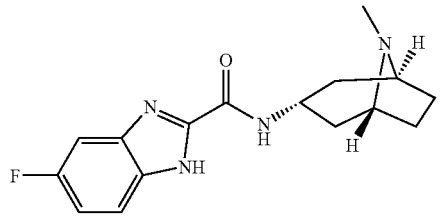

5-Fluoro-1H-benzoimidazole-2-carboxylic acid (8-methyl-8-aza-bicyclo[3.2.1]oct-3-yl)-amide The reaction was carried out as described in General Procedure 2 using 5-fluoro-2-trichloromethyl-1H-benzoimidazole (Example 29, Step A, 100 mg, 0.39 mmol) and 8-methyl- 8-azabicyclo[3.2.1]octan-3-amine dihydrochloride (168 mg, 0.79 mmol). Purification afforded 17 mg (15%) of the title compound. MS (ESI): mass calculated for $C_{16}H_{19}FN_4O$, 302.15; m/z found, 303.2 [M+H]$^+$. $^1$H NMR (400 MHz, CDCl$_3$): 12.01 (br s, 1H), 8.06 (d, J=7.8 Hz, 1H), 7.73 (br s, 0.6H), 7.47 (br s, 1H), 7.22 (br s, 0.4H), 7.10 (m, 1H), 4.35 (q, J=7.1 Hz, 1H), 3.28-3.25 (m, 2H), 2.41-2.35 (m, 2H), 2.34 (s, 3H), 2.28-2.21 (m, 2H), 2.02-1.97 (m, 2H), 1.88 (d, J=14.4 Hz, 2H).

Example 34

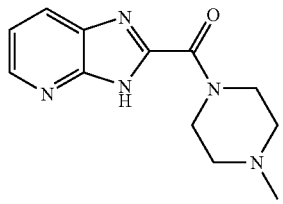

(3H-Imidazo[4,5-b]pyridin-2-yl)-(4-methyl-piperazin-1-yl)-methanone

A. 2-Trichloromethyl-3H-imidazo[4,5-b]pyridine. The reaction was carried out as described in General Procedure 1 using 2,3-diaminopyridine (1.0 g, 9.16 mmol) and methyl-2,2,2-trichloroacidimidate (1.13 mL, 9.16 mmol). Purification on silica gel (40 g; 60% EtOAc/hexanes) afforded 600 mg (28%) of the title intermediate. MS (ESI): mass calculated for $C_7H_4Cl_3N_3$, 234.95; m/z found, 236.0 [M+H]$^+$. $^1$H NMR (400 MHz, CDCl$_3$): 8.65 (dd, J=1.5, 8.1 Hz, 1H), 8.32 (dd, J=1.3, 8.1 Hz, 1H), 7.45 (dd, J=4.8, 8.1 Hz, 1H).

B. (3H-Imidazo[4,5-b]pyridin-2-yl)-(4-methyl-piperazin-1-yl)-methanone. The reaction was carried out as described in General Procedure 2 using 2-trichloromethyl-3H-imidazo[4,5-b]pyridine (100 mg, 0.43 mmol) and N-methylpiperazine (0.09 mL, 0.86 mmol) in THF (3 mL). Purification afforded 29 mg (28%) of the title compound. MS (ESI): mass calculated for $C_{12}H_{15}N_5O$, 245.13; m/z found, 246.2 [M+H]$^+$. $^1$H NMR (400 MHz, CDCl$_3$): 13.63 (s, 1H), 8.71 (d, J=4.3 Hz, 1H), 8.15 (s, 1H), 7.34 (dd, J=4.8, 8.3 Hz, 1H), 4.77 (br s, 2H), 3.96-3.93 (m, 2H), 2.58 (m, 4H), 2.36 (s, 3H).

Example 35

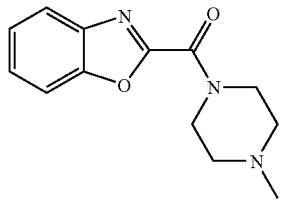

Benzooxazol-2-yl-(4-methyl-piperazin-1-yl)-methanone

General Procedure 3:

A stirred solution of 2-aminophenol (300 mg, 2.75 mmol), methyl 2,2,2-trimethoxyacetate (902 mg, 5.50 mmol), and ytterbium triflate (170 mg, 0.28 mmol) in toluene (10 mL) was heated to reflux. After 5 h, the mixture was cooled, and the precipitate was collected and dried. The crude solid was suspended in toluene (5 mL), and N-methylpiperazine (1.5 mL, 13.7 mmol) was added followed by 2-hydroxypyridine (26 mg, 0.28 mmol). The mixture was heated to 125° C. in a sealed tube for 4 h. The resulting yellow solution was concentrated under reduced pressure, and the residue was purified on silica gel (12 g; 2% methanol/dichloromethane), yielding 320 mg (48%) of the title compound. MS (ESI): mass calculated for $C_{13}H_{15}N_3O_2$, 245.12; m/z found, 246.1 [M+H]$^+$. $^1$H NMR (400 MHz, CDCl$_3$): 7.83-7.79 (m, 1H), 7.66-7.65 (m, 2H), 7.47-7.41 (m, 2H), 4.19 (t, J=5.1 Hz, 4H), 3.88 (t, J=5.1 Hz, 4H), 2.55-2.52 (m, 4H), 2.35 (s, 3H). $^{13}$C NMR (400 MHz, CDCl$_3$): 156.1, 154.6, 149.9, 140.1, 127.1, 125.3, 121.3, 111.5, 55.3, 54.6, 46.9, 45.9, 42.8.

Example 36

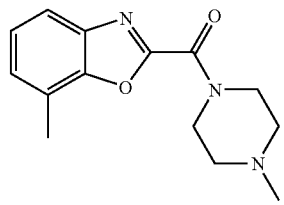

(7-Methyl-benzooxazol-2-yl)-(4-methyl-piperazin-1-yl)-methanone

The reaction sequence was carried out as described in General Procedure 3 starting with 2-amino-6-methyl-phenol (300 mg, 2.43 mmol). Purification afforded 410 mg (65%) of the title compound. MS (ESI): mass calculated for $C_{14}H_{17}N_3O_2$, 259.13; m/z found, 260.2 [M+H]$^+$. $^1$H NMR (400 MHz, CDCl$_3$): 7.66 (d, J=8.1 Hz, 1H), 7.43 (s, 1H), 7.23 (dd, J=8.1, 1.0 Hz, 1H), 4.22 (t, J=5.1 Hz, 4H), 3.88 (t, J=5.1 Hz, 4H), 2.54-2.52 (m, 7H), 2.35 (s, 3H). $^{13}$C NMR (400 MHz, CDCl$_3$): 156.2, 154.4, 150.2, 138.0, 137.9, 126.7, 120.6, 111.5, 55.4, 54.6, 46.9, 46.0, 42.8, 21.9.

Example 37

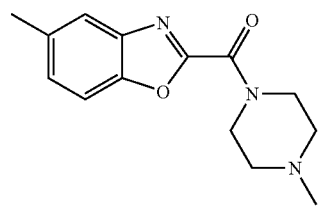

(5-Methyl-benzooxazol-2-yl)-(4-methyl-piperazin-1-yl)-methanone

The reaction sequence was carried out as described in General Procedure 3 starting with 2-amino-4-methyl-phenol (300 mg, 2.43 mmol). Purification afforded 212 mg (34%) of the title compound. MS (ESI): mass calculated for $C_{14}H_{17}N_3O_2$, 259.13; m/z found, 260.2 [M+H]$^+$. $^1$H NMR (400 MHz, CDCl$_3$): 7.47 (s, 1H), 7.40 (d, J=8.3 Hz, 1H), 7.16 (dd, J=8.3, 1.7 Hz, 1H), 4.08 (t, J=5.1 Hz, 4H), 3.76 (t, J=5.1 Hz, 4H), 2.43-2.40 (m, 4H), 2.38 (s, 3H), 2.24 (s, 3H). $^{13}$C NMR (400 MHz, CDCl$_3$): 156.5, 155.3, 158.5, 140.7, 135.5, 128.7, 121.3, 111.2, 55.7, 54.69, 47.2, 46.3, 43.2, 21.8.

Example 38

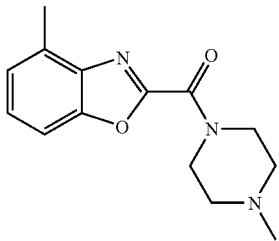

(4-Methyl-benzooxazol-2-yl)-(4-methyl-piperazin-1-yl)-methanone

The reaction sequence was carried out as described in General Procedure 3 starting with 2-amino-3-methyl-phenol (300 mg, 2.43 mmol). Purification afforded 230 mg (37%) of the title compound. MS (ESI): mass calculated for $C_{14}H_{17}N_3O_2$, 259.13; m/z found, 260.2 [M+H]$^+$. $^1$H NMR (400 MHz, CDCl$_3$): 7.37 (d, J=8.1 Hz, 1H), 7.27 (t, J=8.1 Hz, 1H), 7.13 (d, J=8.1 Hz, 1H), 4.12 (t, J=5.1 Hz, 4H), 3.81 (t, J=5.1 Hz, 4H), 2.56 (s, 3H), 2.48-2.44 (m, 4H), 2.28 (s, 3H). $^{13}$C NMR (400 MHz, CDCl$_3$): 156.7, 154.6, 150.1, 139.9, 132.3, 127.2, 126.0, 109.1, 55.7, 54.9, 47.3, 46.3, 43.2, 16.8.

Example 39

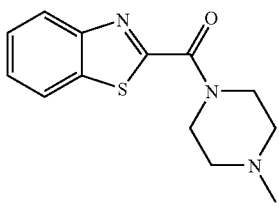

Benzothiazol-2-yl-(4-methyl-piperazin-1-yl)-methanone

A. Benzothiazole-2-carboxylic acid methyl ester. A stirred solution of 2-aminothiophenol (1.70 mL, 15.9 mmol), methyl 2,2,2-trimethoxyacetate (3.93 g, 23.9 mmol), and ytterbium triflate (620 mg, 1.59 mmol) in toluene (10 mL) was heated to reflux. After 1.5 h, the mixture was cooled, and the solvent was removed under reduced pressure. The crude oil was purified on silica gel (40 g; 20-100% ethylacetate/hexanes) to give 2.00 g (66%) of the title intermediate. MS (ESI): mass calculated for $C_9H_7NO_2S$, 193.02; m/z found, 194.1 [M+H]$^+$, 216.0 [M+Na]$^+$. $^1$H NMR (400 MHz, CDCl$_3$): 7.58-7.54 (m, 1H), 7.37-7.35 (m, 2H), 6.95-6.87 (m, 2H), 3.37 (s, 3H). $^{13}$C NMR (400 MHz, CDCl$_3$): 164.82, 162.5, 156.9, 140.7, 131.9, 131.4, 128.6, 126.5, 57.0.

B. Benzothiazol-2-yl-(4-methyl-piperazin-1-yl)-methanone. A mixture of benzothiazole-2-carboxylic acid methyl ester (100 mg, 0.52 mmol), N-methylpiperazine (0.29 mL, 2.59 mmol), and 2-hydroxypyridine (5 mg, 0.05 mmol) in toluene (1.5 mL) was heated in the microwave to 170° C. for 10 min. The resulting yellow solution was concentrated under reduced pressure, and the residue was purified by reversed-phase HPLC, yielding 50 mg (19%) of the title compound as the trifluoroacetate salt. $^1$H NMR (400 MHz, CDCl$_3$): 8.11-8.08 (m, 1H), 7.97-7.96 (m, 2H), 7.55-7.45 (m, 2H), 4.45 (t, J=5.1 Hz, 4H), 3.88 (t, J=5.1 Hz, 4H), 2.55-2.52 (m, 4H), 2.35 (s, 3H). $^{13}$C NMR (400 MHz, CDCl$_3$): 164.7, 159.7, 153.0, 136.1, 126.6, 126.5, 124.6, 121.8, 55.5, 54.7, 46.4, 46.0, 43.5.

Example 40

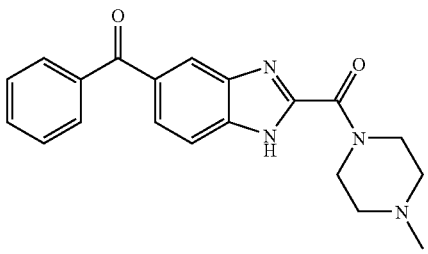

(5-Benzoyl-1H-benzoimidazol-2-yl)-(4-methyl-piperazin-1-yl)-methanone

A. (2-Hydroxymethyl-1H-benzoimidazol-5-yl)-phenyl-methanone. A mixture of (3,4-diamino-phenyl)-phenyl-methanone (4.28 g, 20.16 mmol) and glycolic acid (5 mL, 70% solution in water) in 4 N HCl (40 mL) was heated to 100° C. for 2 h. The warm mixture was poured into water (350 mL) and allowed to cool. Neutralization with concentrated NH$_4$OH resulted in the formation of a solid, which was collected by filtration, washed with water and dried under vacuum to reveal 4.99 g (98%) of the title intermediate. MS (ESI): mass calculated for $C_{15}H_{12}N_2O_2$, 252.09; m/z found, 253.1 [M+H]$^+$. $^1$H NMR (400 MHz, CD$_3$OD): 8.02-7.99 (m, 1H), 7.79-773 (m, 3H), 7.66-7.62 (m, 2H), 7.56-7.51 (m, 2H), 4.90 (br, 4H).

B. (5-Benzoyl-1H-benzoimidazol-2-yl)-(4-methyl-piperazin-1-yl)-methanone. To a suspension of (2-Hydroxymethyl-1H-benzoimidazol-5-yl)-phenyl-methanone (2.0 g, 7.9 mmol) in water (250 mL) was added 2 M Na$_2$CO$_3$ (10 mL). To the mixture was added dropwise a 0.1 M solution of KMnO4 (1.9 g, 12.0 mmol). This mixture was heated to 100° C. for 2 h and was then filtered while hot, and the cooled filtrate was acidified with 3 N acetic acid. The resulting solids were collected by filtration, washed with water and dried under vacuum. The crude acid (0.63 g, 30%) was used in the amide coupling without further purification. To a suspension of the acid (120.7 mg, 0.45 mmol) in DMF (3 mL) was added CDI (82.3 mg, 0.51 mmol), and this mixture was stirred for 1 h. N-methyl piperazine was then added (55 μL), and the reaction mixture was stirred at room temperature for 16 h. The mixture was poured into water (50 mL) and extracted with dichloromethane. The combined extracts were concentrated under reduced pressure, and the residue was purified on silica gel (10 g; 1-8% methanol (2 M NH$_3$)/dichloromethane) to reveal 71.8 mg (45%) of an off-white solid. MS (ESI): mass calculated for $C_{20}H_{20}N_4O_2$, 348.16; m/z found, 349.1 [M+H]$^+$. $^1$H NMR (400 MHz, CDCl$_3$): 12.21 (b s, 1H), 8.25-8.22 (m, 0.5H), 7.93-7.91 (m, 1.5H), 7.83-7.79 (m, 2H), 7.62-7.56 (m, 1H), 7.51-7.46 (m, 2H), 4.83-4.73 (m, 2H), 3.96-3.93 (m, 2H), 2.61-2.59 (m, 2H), 2.56-2.53 (m, 2H), 2.36 (s, 3H).

Example 41

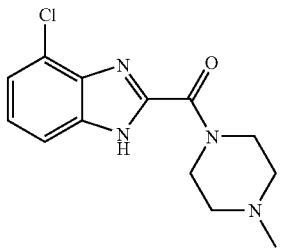

(4-Chloro-1H-benzoimidazol-2-yl)-(4-methyl-piperazin-1-yl)-methanone

A. 4-Chloro-2-trichloromethyl-1H-benzoimidazole. The reaction was carried out as described in General Procedure 1 with 3-chloro-1,2-phenylenediamine (647 mg, 4.52 mmol). After 1.5 h water (10 mL) was added, and the precipitate was collected by filtration to give 1.04 mg (86%) of the title intermediate. MS (ESI): mass calculated for $C_8H_4Cl_4N_2$, 269.9; m/z found, 271.0 [M+H]$^+$.

B. (4-Chloro-1H-benzoimidazol-2-yl)-(4-methyl-piperazin-1-yl)-methanone. The reaction was carried out as described in General Procedure 2 with 4-chloro-2-trichloromethyl-1H-benzoimidazole (1.04 g, 3.86 mmol) and N-methylpiperazine (0.39 mL, 4.25 mmol). Purification afforded 594 mg (56%) of the title compound. MS (ESI): mass calculated for $C_{13}H_{15}ClN_4O$, 278.74; m/z found, 279.5 [M+H]$^+$. $^1$H NMR (400 MHz, CDCl$_3$): 12.3-11.19 (s, 1H), 7.71-7.40 (m, 1H), 7.32 (d, J=7.8 Hz, 1H), 7.23 (d, J=7.8 Hz, 1H), 4.82-4.72 (m, 2H), 3.96-3.93 (m, 2H), 2.60-2.55 (m, 4H), 2.37 (s, 3H).

Example 42

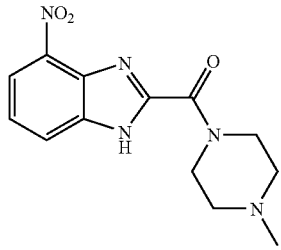

(4-Methyl-piperazin-1-yl)-(4-nitro-1H-benzoimidazol-2-yl)-methanone

A. 4-Nitro-2-trichloromethyl-1H-benzoimidazole. The reaction was carried out as described in General Procedure 1 with 3-nitro-1,2-phenylenediamine (1 g, 6.54 mmol). After 1.5 h water (10 mL) was added and the precipitate was collected by filtration to give 1.18 mg (64%) of the title intermediate. MS (ESI): mass calculated for $C_8H_4Cl_3N_3O_2$, 280.49; m/z found, 281.2 [M+H]$^+$.

B. (4-Methyl-piperazin-1-yl)-(4-nitro-1 H-benzoimidazol-2-yl)-methanone. The reaction was carried out as described in General Procedure 2 with 4-nitro-2-trichloromethyl-1H-benzoimidazole (1.18 g, 4.20 mmol) and N-methylpiperazine (0.70 mL, 6.30 mmol). Purification afforded 801 mg (66%) of the title compound. MS (ESI): mass calculated for $C_{13}H_{15}N_5O_3$, 289.29; m/z found, 290.3 [M+H]$^+$. $^1$H NMR (400 MHz, CDCl$_3$): 11.36-11.24 (s, 1H), 8.29 (d, J=7.8 Hz, 1H), 8.17 (d, J=7.8 Hz, 1H), 7.45 (t, J=7.8 Hz, 1H), 4.71-4.68 (m, 2H), 3.92-3.89 (m, 2H), 2.58-2.54 (m, 4H), 2.37 (s, 3H).

Example 43

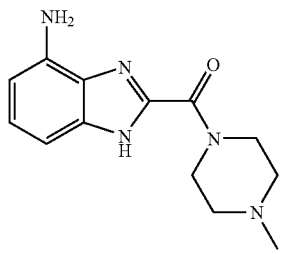

(4-Amino-1H-benzoimidazol-2-yl)-(4-methyl-piperazin-1-yl)-methanone

To a solution of (4-methyl-piperazin-1-yl)-(4-nitro-1H-benzoimidazol-2-yl)-methanone (640 mg, 2.21 mmol) in 1:1 THF/ethanol (10 mL, with a few drops of ethyl acetate) was added 10% palladium on carbon (640 mg). The reaction mixture was placed under 1 atm hydrogen for 72 h. The resulting mixture was filtered through diatomaceous earth, and the filtrate was concentrated under reduced pressure. The crude product was purified on silica gel (40 g; 0-10% methanol/CH$_2$Cl$_2$) to afford 519 mg (91%) of the title compound. MS (ESI): mass calculated for $C_{13}H_{17}N_5O$, 259.31; m/z found, 260.3 [M+H]$^+$. $^1$H NMR (400 MHz, CDCl$_3$): 12.21-11.36 (s, 1H), 7.12 (t, J=7.8 Hz, 1H), 6.94-6.83 (m, 1H), 6.53 (d, J=7.8 Hz, 1H), 4.82-4.78 (m, 2H), 4.43-4.40 (m, 2H), 3.94-3.92 (m, 2H), 2.56-2.54 (m, 4H), 2.35 (s, 3H).

Example 44

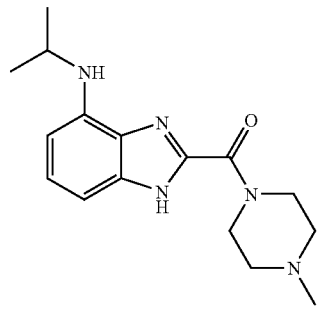

(4-Isopropylamino-1 H-benzoimidazol-2-yl)-(4-methyl-piperazin-1-yl)-methanone

To a solution of (4-amino-1H-benzoimidazol-2-yl)-(4-methyl-piperazin-1-yl)-methanone (Example 43; 50 mg, 0.19 mmol) in dichloroethane (10 mL), was added acetone (0.07 mL, 0.96 mmol) and acetic acid (10 drops), followed by NaBH(OAc)$_3$ (203 mg, 0.96 mmol). The reaction mixture was stirred at room temperature for 16 h, and then was quenched with satd aq NaHCO$_3$ (5 mL). The aqueous layer was extracted with CHCl$_3$ (10 mL), and the combined organic layers were dried (Na$_2$SO$_4$) and then concentrated under reduced pressure. The crude product was purified on silica gel (10 g; 0-10% methanol (2 M NH$_3$)/CH$_2$Cl$_2$) to give 35 mg of the title compound (60%). MS (ESI): mass calculated for $C_{16}H_{23}N_5O$, 301.39; m/z found, 302.3 [M+H]$^+$. $^1$H NMR (400 MHz, CDCl$_3$): 11.11-11.07 (s, 1H), 7.18 (t, J=7.8 Hz, 1H), 6.76 (d, J=7.8 Hz, 1H), 6.37 (d, J=7.8 Hz, 1H), 4.80-4.65 (m, 2H), 3.92-3.78 (m, 2H), 2.56-2.53 (m, 4H), 2.36 (s, 3H), 1.85-1.81, (m, 1H), 1.32 (d, J=6.3 Hz, 6H).

Example 45

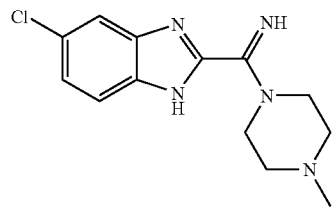

C-(5-Chloro-1H-benzoimidazol-2-yl)-C-(4-methyl-piperazin-1-yl)-methyleneamine

To a suspension of 5-chloro-2-trichloromethyl-1H-benzoimidazole (100 mg, 0.37 mmol) in acetonitrile (4 mL) was added N-methylpiperazine (0.04 mL, 0.4 mmol). The mixture was stirred for 10 min then ammonium acetate (29 mg, 0.38 mmol) was added. After 18 h the reaction mixture was diluted with satd aq $NaHCO_3$ (10 mL), and then extracted with dichloromethane (3×10 mL). The combined extracts were dried ($Na_2SO_4$) and then concentrated under reduced pressure. The crude product was purified on silica gel (10 g; 0-10% methanol (2 M $NH_3$)/dichloromethane) to afford 23 mg (22%) of the title compound. MS (ESI): mass calculated for $C_{13}H_{16}N_4O$, 277.11; m/z found, 278.2 [M+H]$^+$. $^1$H NMR (400 MHz, $CD_3OD$): 7.79-7.74 (m, 2H)$_1$ 7.45 (dd, J=8.6, 2.0 Hz, 1H), 4.23-4.17 (m, 4H), 3.63-3.58 (m, 4H), 3.01 (s, 3H).

Biological Examples

Binding Assay on Recombinant Human Histamine $H_4$ Receptor

SK-N-MC cells or COS7 cells were transiently transfected with pH 4R and grown in 150 cm$^2$ tissue culture dishes. Cells were washed with saline solution, scraped with a cell scraper and collected by centrifugation (1000 rpm, 5 min). Cell membranes were prepared by homogenization of the cell pellet in 20 mM Tris-HCl with a polytron tissue homogenizer for 10 s at high speed. Homogenate was centrifuged at 1000 rpm for 5 min at 4° C. The supernatant was then collected and centrifuged at 20,000×g for 25 min at 4° C. The final pellet was resuspended in 50 mM Tris-HCl. Cell membranes were incubated with H-histamine (5-70 nM) in the presence or absence of excess histamine (10000 nM). Incubation occurred at room temperature for 45 min. Membranes were harvested by rapid filtration over Whatman GF/C filters and washed 4 time with ice-cold 50 mM Tris HCl. Filters were then dried, mixed with scintillant and counted for radioactivity. SK-N-MC or COS7 cells expressing human histamine $H_4$ receptor were used to measure the affinity of binding of other compounds and their ability to displace $^3$H-ligand binding by incubating the above-described reaction in the presence of various concentrations of inhibitor compound to be tested. For competition binding studies using $^3$H-histamine, $K_i$ values were calculated, based on an experimentally determined $K_D$ value of 5 nM and a ligand concentration of 5 nM, according to Y.-C. Cheng and W. H. Prusoff (*Biochem. Pharmacol.* 1973, 22(23):3099-3108): $K_i=(IC_{50})/(1+([L]/(K_D)))$.

| BINDING ASSAY RESULTS | |
|---|---|
| EX | $K_i$ (nM) |
| 1 | 32 |
| 2 | 490 |
| 3 | 331 |
| 4 | 1400 |
| 5 | 89 |
| 6 | 25 |
| 7 | 87 |
| 8 | 300 |
| 9 | 28 |
| 10 | 620 |
| 11 | 355 |
| 12 | 807 |
| 13 | 380 |
| 14 | 53 |
| 15 | 216 |
| 16 | 1300 |
| 17 | 535 |
| 18 | 226 |
| 19 | 1000 |
| 20 | 156 |

-continued

| BINDING ASSAY RESULTS | |
|---|---|
| EX | $K_i$ (nM) |
| 21 | 468 |
| 22 | 31 |
| 23 | 135 |
| 24 | 270 |
| 25 | 613 |
| 26 | 528 |
| 27 | 11 |
| 28 | 420 |
| 29 | 26 |
| 30 | 370 |
| 31 | 42 |
| 32 | 460 |
| 34 | 833 |
| 35 | 620 |
| 36 | 1200 |
| 37 | 1300 |
| 38 | 1600 |
| 39 | 810 |
| 40 | 8000 |
| 41 | 57 |
| 45 | 110 |
| 46 | 64 |
| 47 | 158 |
| 48 | 23 |
| 49 | 51 |

Mast Cell Chemotaxis Assay

Mast cell accumulation in mucosal epithelia is a well-known characteristic of allergic rhinitis and asthma. Transwells (Costar, Cambridge, Mass.) of a pore size 8 μm were coated with 100 μL of 100 ng/mL human fibronectin (Sigma) for 2 h at room temperature. After removal of the fibronectin, 600 μL of RPMI with 5% BSA, in the presence of 10 μM histamine, was added to the bottom chamber. To test the various histamine receptor (HR) antagonists, 10 μM and/or 1 μM solutions of the test compounds were added to the top and bottom chambers. Mast cells (2×10$^5$/well) were added to the top chamber. The plates were incubated for 3 h at 37° C. Transwells were removed, and the cells in the bottom chamber were counted for sixty seconds using a flow cytometer.

| 10 μM Histamine | HR Antagonist (μM): | | | | Binding Assay |
|---|---|---|---|---|---|
| | 10 | | 1 | | |
| EX | % Inh | Stdev | % Inh | Stdev | $K_i$ (nM) |
| 9 | 97 | | 72 | 11 | 28 |
| 6 | 97 | 1 | 84 | 5 | 25 |
| 7 | 101 | 1 | 8 | 15 | 87 |
| 25 | 27 | 75 | 66 | 12 | 613 |

Cell-Type Distribution of $H_4$ Expression

RNA was prepared from the different cells using an RNeasy kit (Qiagen, Valencia, Calif.) according to the manufacturer's instructions. RNA samples (5 μg) were run on an RNA gel and then transferred overnight to a nylon blot (Hybond, Amersham Pharmacia Biotech, Piscataway, N.J.). The blot was pre-hybridized with ExpressHyb solution (CLONTECH) for 30 min at 68° C. The $H_4$ receptor DNA was labeled using the Rediprime II kit (Amersham Pharmacia Biotech). The blot was hybridized for 2 h at 68° C., followed by one wash step (23 SSC and 0.05% SDS) of 40 min at room temperature, and a second wash step (0.13 SSC and 0.1%

SDS) of 40 min at 50° C. The blot was exposed to X-ray film at −70° C. with two intensifying screens overnight.

Results

The Northern Blot results indicate that the $H_4$ receptor is expressed on bone marrow-derived mast cells (BMMC), peritoneal mast cells, and eosinophils. These positive results are consistent with the published literature (e.g. Oda et al., Nguyen et al., and Morse et al. in the Background section). However, the negative results of the Northern Blot experiment, such as the finding of apparently no measurable levels of $H_4$ receptor expressed by neutrophils, differ somewhat from the above literature findings. This may be explained by the different methodologies used. Accumulation of mast cells and eosinophils in affected tissues is one of the principal characteristics of allergic rhinitis and asthma. Since $H_4$ receptor expression is limited to these cell types; $H_4$ receptor signaling is likely to mediate the infiltration of mast cells and eosinophils in response to histamine. Additional investigation may also clarify these issues. The following table reports the Cell-type Distribution of $H_4$ Expression by Northern Blot.

| Species | Cell Type | $H_4$ |
|---|---|---|
| Human | Eosinophils | + |
|  | Immature Dendritic Cells | − |
|  | Mature Dendritic Cells | − |
|  | CD14+ Monocytes | − |
|  | CD4+ T Cells | − |
|  | CD8+ T Cells | − |
|  | B Cells | − |
|  | Neutrophils | − |
| Mouse/(Rat) | Eosinophils | + |
|  | Peritoneal Mast Cells (Rat) | + |
|  | BMMC | + |
|  | BM Derived Macrophages | − |
|  | Peritoneal Macrophages | − |
|  | CD4+ T Cells | − |
|  | B Cells | − |

The Inhibition of Eosinophil Shape Change by Histamine $H_4$ Receptor Antagonists Eosinophil accumulation in sites of allergic reaction is a well-known characteristic of allergic rhinitis and asthma. This example demonstrates that histamine $H_4$ receptor antagonists can block the shape change response in human eosinophils in response to histamine. Shape change is a cellular characteristic that precedes eosinophil chemotaxis.

Methods

Human granulocytes were isolated from human blood by a Ficoll gradient. The red blood cells were lysed with 5-10X Qiagen lysis buffer at room temperature for 5-7 min. Granulocytes were harvested and washed once with FACS buffer. The cells were resuspended at a density of $2 \times 10^6$ cells/mL in reaction buffer. To test inhibition by specific histamine receptor antagonists, 90 µL of the cell suspension (~$2 \times 10^5$ cells) was incubated with 10 µM of one of the various test compound solutions. After 30 min, 11 µL of one of the various concentrations of histamine was added. Ten minutes later the cells were transferred to ice and fixed with 250 µL of ice-cold fixative buffer (2% formaldehyde) for 1 min. The shape change was quantitated using a gated autofluoescence forward scatter assay (GAFS) (Byran et al., Am. J. Crit. Care Med. 2002, 165:1602-1609).

Results—Histamine Mediates Eosinophil Shape Change through $H_4$ Receptor

The change in shape of eosinophils is due to cytoskeletal changes that precede chemotaxis and thus is a measure of chemotaxis. The data in the following table show that histamine induces a dose-dependent shape change in eosinophils. Histamine receptor (HR) antagonists were used to sort out which histamine receptor is responsible for the shape change. Antagonists specific for the histamine $H_1$ receptor (diphenhydramine) or the $H_2$ receptor (ranatidine) did not alter the histamine-induced shape change. However, a dual $H_3/H_4$ antagonist (thioperamide) and a specific histamine $H_4$ receptor antagonist ((5-Chloro-1H-indol-2-yl)-(4-methyl-piperazin-1-yl)-methanone, $K_i$=5 nM) inhibited histamine-induced eosinophil shape change with an $IC_{50}$ of 1.5 and 0.27 µM, respectively.

|  | Fold Change | | | | |
|---|---|---|---|---|---|
|  | 10 | 1 | 0.1 | 0.01 | 0 |
| Histamine (µM): | | | | | |
| No HR Antagonist | 1.34 | 1.31 | 1.21 | 1.01 | 1.00 |
| 10 µM $H_4$ Antagonist | 1.09 | 1.05 | 1.05 | 1.01 | 1.00 |
| 10 µM Thiop | 1.08 | 1.05 | 1.01 | 1.04 | 1.00 |
| 10 µM Diphen | 1.63 | 1.50 | 1.18 | 1.03 | 1.00 |
| 10 µM Ranat | 1.64 | 1.49 | 1.21 | 1.04 | 1.00 |

The Inhibition of Eosinophil Chemotaxis by Histamine $H_4$ Receptor Antagonists

Eosinophil accumulation in sites of allergic reaction is a well-known characteristic of allergic rhinitis and asthma. Eosinophils are purified from human blood with standard methods. Chemotaxis assays are carried out using transwells (Costar, Cambridge, Mass.) of a pore size 5 µm coated with 100 µL of 100 ng/mL human fibronectin (Sigma) for 2 h at room temperature. After removal of the fibronectin, 600 µL of RPMI with 5% BSA in the presence of histamine (ranging from 1.25-20 µM) is added to the bottom chamber. To test the various histamine receptor antagonists 10 µM of the test compounds can be added to the top and bottom chambers. Eosinophils will be added to the top chamber whereas histamine or chemotactic factors will be placed in the lower chamber. The plates are incubated for 3 h at 37° C. Transwells are removed and the number of cells in the bottom chamber can be counted for 60 s using a flow cytometer, or can be quantitated by using Giemsa staining.

The Inhibition of Zymosan-Induced Peritonitis in Mice by Histamine $H_4$ Receptor Antagonists It has been demonstrated that histamine $H_4$ receptor antagonists can block the peritonitis induced by zymosan, which is the insoluble polysaccharide component on the cell wall of *Saccharomyces cerevisiae*. This is commonly used to induce peritonitis in mice and appears to act in a mast cell-dependent manner. Compounds of the present invention can be tested in such a model to demonstrate their use as anti-inflammatory agents. At time 0 mice are given compound or PBS, either s.c. or p.o. Fifteen minutes later each mouse receives 1 mg zymosan A (Sigma) i.p. The mice are sacrificed 4 h later, and the peritoneal cavities are washed with 3 mL of PBS containing 3 mM EDTA. The number of migrated leukocytes is determined by taking an aliquot (100 µL) of the lavage fluid and diluting 1:10 in Turk's solution (0.01% crystal violet in 3% acetic acid). The samples are then vortexed, and 10 µL of the stained cell solution is placed in a Neubauer haemocytometer. Differential cell counts are performed using a light microscope (Olympus B061). In view of their chromatic characteristics and their nucleus and cytoplasm appearance, polymorphonuclear leukocytes (PMN; >95% neutrophils) can be easily identified. Treatment with zymosan increases the number of neutrophils, which is representative of an inflammatory response. Treatment with $H_4$ receptor antagonist will block this incease.

Inhibition of Mast Cell Chemotaxis by $H_4$ Receptor Antagonist in an Animal Model of Asthma and Allergic Rhinitis An animal model will be used to test the observation that mast cells accumulate in response to allergic inflammation, and that this can be blocked by $H_4$ receptor antagonists. Compounds of the present invention can be tested in this model to demonstrate their use as treatments for allergic rhinitis or asthma. Mice will be sensitized by intraperitoneal injection of ovalbumin/Alum (10 μg in 0.2 ml Al(OH)$_3$; 2%) on Day 0 and Day 14. On Day 21 through 23 mice will be challenged by PBS or ovalbumin, and sacrificed 24 h after the last challenge on Day 24. A section of the trachea will be removed and fixed in formalin. Paraffin embedding and longitudinal sectioning of tracheas will be performed followed by staining of mast cells with toluidine blue. Alternatively, trachea will be frozen in OCT for frozen sectioning, and mast cells will be identified by IgE staining. Mast cells will be quantified as sub-mucosal or sub-epithelial depending on their location within each tracheal section. Exposure to allergen should increase the number of sub-epithelial mast cells, and this effect will be blocked by $H_4$ receptor antagonists.

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety. These other embodiments are also within the scope of the invention.

What is claimed is:

1. A compound of formula (I):

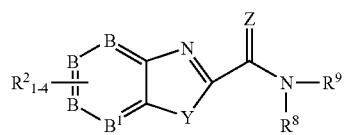

wherein
B and $B^1$ are C;
Y is $NR^z$, where $R^z$ is H or $C_{1-4}$alky;
Z is O or S;
$R^8$ H and $R^9$ is

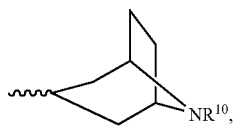

where $R^{10}$ is H or $C_{1-4}$alky, or $R^8$ and $R^9$ are taken together with their N of attachment to form

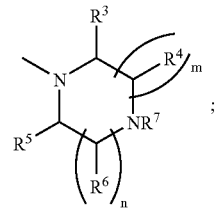

n is 1 or 2;
m is 1 or 2;
n +m is 2 or 3;
$R^2$ are independently, F, Br, I, $C_{1-4}$alkyl, $C_{1-4}$alkoxy, $C_{3-6}$cycloalkyl, —O$C_{3-6}$cycloalkyl, —OCH$_2$Ph, —CF$_3$, —OCF$_3$, —SCF$_3$, —OH, —(C=O)$R^k$ (wherein $R^k$ is H, $C_{1-4}$alkyl, —OH, phenyl, benzyl, phenethyl or $C_{1-6}$alkoxy), —(N—$R^t$)(C=O)$R^k$ (where $R^t$ is H or $C_{1-4}$alkyl), —(N—$^t$)SO$_2$C$_{1-4}$alkyl, —(S=(O)$_p$)—$C_{1-4}$ alkyl (wherein p is 0, 1 or 2), nitro, —N$R^l R^m$ (wherein $R^l$ and $R^m$ are independently selected from H, $C_{1-4}$alkyl, phenyl, benzyl or phenethyl, or $R^l$ and $R^m$ taken together with the nitrogen to which they are attached, form a 4-7 membered heterocyclic ring with 0 or 1 additional heteroatoms selected from O, S, NH or NC$_{1-4}$alkyl), —SO$_2$N$R^l R^m$, —(C=O)N$R^l R^m$, cyano or phenyl, where any phenyl or alkyl or cycloalkyl moiety of the foregoing is optionally and independently substituted with between 1 and 3 substituents selected from $C_{1-3}$alkyl, halo, hydroxy, amino, and $C_{1-3}$alkoxy;
$R^3$ and $R^4$ are, independently, H, $C_{1-4}$alkyl, $C_{3-6}$cycloalkyl, $C_{1-4}$alkyl($C_{3-6}$cycloalkyl), cyano, —CF$_3$, —(CO)N$R^p R^q$, —(CO)O$R^r$, —CH$_2$N$R^p R^q$ or —CH$_2$O$R^r$; where $R^p$, $R^q$ and $R^r$ independently selected from H, $C_{1-4}$alkyl, $C_{3-6}$cycloalkyl, phenyl, —$C_{1-2}$alkyl($C_{3-6}$cycloalkyl), benzyl or phenethyl, or $R^p$ and $R^q$ taken together with the nitrogen to which they are attached, form a 4-7 membered heterocyclic ring with 0 or 1 additional heteroatoms selected from O, S, NH or NC$_{1-6}$alkyl, and where any phenyl or alkyl or cycloalkyl moiety of the forgoing is optionally and independently substituted with between 1 and 3 substituents selected from $C_{1-3}$alkyl, halo, hydroxy, amino, and $C_{1-3}$alkoxy;
$R^5$ and $R^6$ are, independently, H or $C_{1-6}$alkyl;
$R^7$ is —$R^a$, —$R^b R^a$, —$R^e$—O—$R^a$ or —$R^e$-N($R^c$)($R^d$), where $R^a$ is H, cyano, —(C=O)N($R^c$)($R^d$), —C(=NH)(NH$_2$), $C_{1-10}$alkyl, $C_{2-8}$alkenyl, $C_{3-8}$cycloalkyl, $C_{4-7}$heterocyclic radical or phenyl, where the $C_{4-7}$heterocyclic radical is attached at a carbon atom and contains one of O, S, NH or NC$_{1-4}$alkyl, and optionally an additional NH or NC$_{1-6}$alkyl in ring of 5 or 6 or 7 members, where $R^b$ is $C_{1-8}$alkylene or $C_{2-8}$alkenylene, where $R^e$ is $C_{2-8}$alkylene or $C_{2-8}$alkenylene, where $R^c$ and $R^d$ are each independently H, $C_{1-4}$alkyl, $C_{2-4}$alkenyl, $C_{3-6}$cycloalkyl or phenyl, or $R^c$ and $R^d$ taken together with the nitrogen to which they are attached, form a 4-7 membered heterocyclic ring with 0 or 1 additional heteroatoms selected from O, S, NH or NC$_{1-6}$alkyl, and where any phenyl or alkyl or cycloalkyl moiety of the foregoing is optionally and independently substituted with between 1 and 3 substituents selected from $C_{1-3}$alkyl, halo, hydroxy, amino, and $C_{1-3}$alkoxy;
alternatively, $R^7$ may be taken together with an adjacent $R^4$ as well as their carbon and nitrogen of attachment to form a 5, 6 or 7 membered heterocyclic ring, with 0 or 1 additional heteroatoms selected from O, S, NH or HC$_{1-6}$ alkyl, and optionally and independently substituted with between 1 and 3 substituents selected from C$_{1-3}$alkyl, halo, hydroxy, amino, and C$_{1-3}$alkoxy;

alternatively, R$^7$ may be taken together with an adjacent R$^4$ as well as their carbon and nitrogen of attachment to form a 5, 6 or 7 membered heterocyclic ring, with 0 or 1 additional heteroatoms selected from O, S NH or NC$_{1-6}$ alkyl, and optionally and independently substituted with between 1 and 3 substituents selected from C$_{1-3}$alkyl, halo, hydroxy, amino, and C$_{1-3}$alkoxy;

and enantiomers, diastereomers and pharmaceutically acceptable salts and esters thereof, with the following provisos, that R$^6$ adjacent to N must be H where R$^4$ adjacent to N is other than H, and that R$^2$ cannot be benzoyl when one of R$^4$ and R$^6$ is methyl and the other is hydrogen.

2. The compound of claim 1 wherein Y is NH.

3. The compound of claim 1 wherein Z is O.

4. The compound of claim 1 wherein R$^{10}$ is H or methyl.

5. The compound of claim 1 wherein n is 1 and m is 1.

6. The compound of claim 1 wherein R$^2$ are, independently, selected from the group consisting of —F, —Br, —I, —CH$_3$, —CH$_2$CH$_3$, —OCH$_3$, —OCH$_2$CH$_3$, —OCH(CH$_3$)$_2$, cyclopropyl, cyclobutyl, cyclopentyl, cyclohexyl, -Ocyclopentyl, -Ocyclohexyl, —CF$_3$, —OCF$_3$, —SCF$_3$, —C(O)CH$_3$, —C(O)CH$_2$CH$_3$, —OH, —COOH, —C(O)phenyl, —C(O)benzyl, —COOCH$_3$, —COOCH$_2$CH$_3$, —NHCOCH$_3$, —NCH$_3$COCH$_3$, —NHSO$_2$CH$_3$, —NCH$_3$SO$_2$CH$_3$, —SOCH$_3$, —SO$_2$CH$_3$, —NO$_2$, —NH$_2$, —NHCH$_3$, —N(CH$_3$)$_2$, —N(CH$_2$CH$_3$)$_2$, —pyrrollidin-1 -yl, -imidazolidin-1 -yl, -pyrazolidin-1 -yl, -piperidin-1 -yl, -piperazin-1 -yl, -morpholin-4-yl, -thiomorpholin-4-yl, —SO$_2$NH$_2$, —SO$_2$NHCH$_3$, —SO$_2$N(CH$_3$)$_2$, —SO$_2$N (CH$_2$CH$_3$)$_2$, —SO$_2$pyrrolidin-1 -yl, —SO$_2$imidazolidin-1 -yl, —SO$_2$pyrazolidin- 1 -yl, —SO$_2$piperidin- 1 -yl, —SO$_2$piperazin- 1 -yl, —SO$_2$morpholin-4-yl, —SO$_2$thiomorpholin-4-yl, —C(O)NH$_2$, —C(O)N(CH$_3$)$_2$, —C(O)NH(CH$_3$), —C(O)N(CH$_2$CH$_3$)$_2$, —C(O)pyrrolidin-1 -yl, —C(O)imidazolidin- 1 -yl, —C(O)pyrazolidin-1-yl, —C(O)piperidin-1 -yl, —C(O)piperazin- 1 -yl, —C(O)morpholin-4-yl, —C(O)thiomorpholin-4-yl, —CN and phenyl.

7. The compound of claim 1 wherein R$^2$ are, independently, selected from the group consisting of methyl, trifluoromethyl, methoxy, trifluoromethoxy, nitro, fluoro and benzoyl.

8. The compound of claim 1 wherein R$^3$ and R$^4$ are, independently, selected from the group consisting of
a) H,
b) —CH$_3$, —CH$_2$CH$_3$, CH$_2$CH$_2$CH$_3$, —CH(CH$_3$)$_2$, n-butyl, i-butyl, t-butyl,
c) cyclopropyl, cyclopentyl, cyclohexyl, —CH$_2$cyclopropyl, —CH$_2$cyclopentyl, —CH$_2$cyclohexyl, —CH2Ocyclopropyl, —CH$_2$Ocyclopentyl, —CH$_2$Ocyclohexyl,
d) cyano,
e) trifluoromethyl,
f) —(C═O)NH$_2$, —(C═O)NHC$_{1-4}$alkyl, —(C═O)N (C$_{1-4}$alkyl)$_2$, —(C═O)NHphenyl, —(C═O)pyrrolidin-1 -yl, —(C═O)imidazolidin- 1 -yl, —(C═O)pyrazolidin-1 -yl, —(C═O)piperidin-1 -yl, —(C═O)piperazin-1 -yl, —(C═O)morpholin-4-yl, —(C═O)thiomorpholin-4-yl,
g) —COOH, —COOCH$_3$, —COOCH$_2$CH$_3$, —COOphenyl, —COObenzyl,
h) —CH$_2$NH$_2$, —CH$_2$NHC$_{1-4}$alkyl, —CH$_2$N (C$_{1-4}$alkyl)$_2$, —CH$_2$NHphenyl, —CH$_2$NHbenzyl, -CH$_2$pyrrolidin-1 -yl, —CH$_2$imidazolidin-1 -yl, -CH$_2$pyrazolidin-1 -yl, —CH$_2$piperidin -1 -yl, —CH$_2$piperazin-1 -yl, —CH$_2$morpholin-4-yl, —CH$_2$thiomorpholin-4-yl,
i) —CH$_2$OH, —CH$_2$CH$_2$OH, —CH$_2$CH$_2$CH$_2$OH, —CH$_2$OCH$_3$, —CH$_2$OCH$_2$CH$_3$, —CH$_2$OCH$_2$CH$_2$CH$_3$, —CH$_2$OCH(CH$_3$)$_2$, —CH$_2$O-n-butyl, —CH$_2$O-i-butyl, —CH$_2$O-t-butyl, —CH$_2$Ophenyl, —CH$_2$Obenzyl and —CH$_2$ $_{OCH2}$ cyclopropyl.

9. The compound of claim 1 wherein R$^3$ and R$^4$ are, independently, H or —CH$_3$.

10. The compound of claim 1 wherein R$^5$ and R$^6$ are, independently, selected from the group consisting of H and methyl.

11. The compound of claim 1 wherein R5 and R$^6$ are H.

12. The compound of claim 1 wherein R$_7$ is selected from the group consisting of
a) H, —CH$_2$CH$_2$OH, —CH$_2$CH$_2$CH$_2$OH,
b) cyano,
c) —(C═O)NH$_2$, —(C═O)NHC$_{1-4}$alkyl, —(C═O)N (C$_{1-4}$alkyl)$_2$, (C═O)NHphenyl, —(C═O)pyrrolidin-1 -yl, —(C═O)imidazolidin-1 -yl, —(C═O)pyrazolidin-1-yl, —(C═O)piperidin-1-yl, —(C═O)piperazin-1-yl, —(C═O)morpholin-4-yl, —(C═O)thiomorpholin-4-yl, —CH$_2$(C═O)NH$_2$, —CH$_2$(C═O) NHC$_{1-4}$alkyl, —CH$_2$(C═O)N(C$_{1-4}$alkyl)$_2$, —CH$_2$(C═O)NHphenyl, —CH$_2$(C═O)pyrrolidin -1-yl, —CH$_2$(C═O)imidazolidin-1-yl, —CH$_2$(C═O)pyrazolidin-1 -yl —CH$_2$(C═O)piperidin-1 -yl, —CH$_2$(C═O)piperazin-1 -yl, —CH$_2$(C═O)morpholin-4-yl, —CH$_2$(C═O)thiomorpholin-4-yl, -CH$_2$CH$_2$O(C═O)NH$_2$, —CH$_2$CH$_2$O(C═O)NHC$_{1-4}$alkyl, —CH$_2$CH$_2$O (C═O)N(C$_{1-4}$alkyl)$_2$, —CH$_2$CH$_2$O(C═O) NHphenyl, —CH$_2$CH$_2$O(C═O)pyrrolidin-1-yl, —CH$_2$CH$_2$O (C═O)imidazolidin-1 -yl, —CH$_2$CH$_2$O(C═O)pyrazolidin-1 -yl, —CH$_2$CH$_2$O(C═O)piperidin-1 -yl, —CH$_2$CH$_2$O(C═O)piperazin-1 -yl, —CH$_2$CH$_2$O (C═C)morpholin-4-yl, —CH$_2$CH$_2$O(C═O)thiomorpholin-4-yl,
d) —C(═NH)(NH$_2$), —CH$_2$C(═NH)(NH$_2$),
e) —CH$_3$, —CH$_2$CH$_3$, —CH$_2$CH$_2$CH$_3$, —CH(CH$_3$)$_2$, n-butyl, i-butyl, t-butyl, —CH$_2$CH$_2$OCH$_3$, —CH$_2$CH$_2$OCH$_2$CH$_3$, —CH$_2$CH$_2$OCH$_2$CH$_2$CH$_3$, —CH$_2$CH$_2$OCH(CH$_3$)$_2$, —CH$_2$CH$_2$O-n-butyl, —CH$_2$CH$_2$O-i-butyl, —CH2CH$_2$O-t-butyl,
f) —CH═CH$_2$, —CH$_2$CH═CH$_2$,
g) cyclopropyl, cyclopentyl, cyclohexyl, —CH$_2$cyclopropyl, —CH$_2$cyclopentyl, —CH$_2$cyclohexyl, —CH$_2$CH$_2$Ocyclopropyl, —CH$_2$CH$_2$Ocyclopentyl, —CH$_2$CH$_2$Ocyclohexyl,
h) pyrrolidinyl, imidazolidinyl, pyrazolidinyl, piperidinyl, piperazinyl, morpholinyl, thiomorpholinyl, —CH$_2$pyrrolidinyl, —CH$_2$imidazolidinyl, —CH$_2$pyrazolidinyl, —CH$_2$piperidinyl, —CH$_2$piperazinyl, —CH2morpholinyl, —CH$_2$thiomorpholinyl,
i) —CH$_2$CH$_2$NH$_2$, —CH$_2$CH$_2$NHC$_{1-4}$alkyl, —CH$_2$CH$_2$N (C$_{1-4}$alkyl)$_2$, —CH$_2$CH$_2$NHphenyl, —CH$_2$CH$_2$pyrrolidin-1 -yl, —CH$_2$CH$_2$imidazolidin-1 -yl, —CH$_2$CH$_2$pyrazolidin-1 -yl, —CH$_2$CH$_2$piperidin-1 -yl, —CH$_2$CH$_2$piperazin-1 -yl, —CH$_2$CH$_2$morpholin-4-yl, —CH$_2$CH$_2$thiomorpholin-4-yl,
j) phenyl, benzyl, phenethyl and benzyloxymethyl.

13. The compound of claim 1 wherein $R^7$ is selected from the group consisting of H, —$CH_3$ and —$CH_2CH_3$.

14. The compound of claim 1 wherein $R^7$ taken together with an adjacent $R^4$ as well as their carbon and nitrogen of attachment are pyrrolidin-1,2-yl, imidazolidin-1,2-yl, imidazolidin-1,5-yl, pyrazolidin-1,5-yl, piperidin-1,2-yl, piperazin-1,2-yl, morpholin-4,5-yl and thiomorpholin-4,5-yl.

15. The compound of claim 1 wherein $R^7$ taken together with an adjacent $R^4$ as well as their carbon and nitrogen of attachment are pyrrolidin-1,2-yl and piperidin-1,2-yl.

16. The compound of claim 1 selected from the group consisting of:
(5,6-Difluoro-1H-benzoimidazol-2-yl)-(4-methyl-piperazin-1-yl) -methanone;
(5,6-Difluoro-1H-benzoimidazol-2-yl)-(4-ethyl-piperazin-1-yl) -methanone;
(5,6-Difluoro-1H-benzoimidazol-2-yl)-(3-methyl-piperazin-1-yl) -methanone;
(5,6-Difluoro-1H-benzoimidazol-2-yl)-(4-methyl-[1,4]diazepan-1-yl) methanone;
5,6-Difluoro-1H-benzoimidazole-2-carboxylic acid (8-methyl-8-aza-bicyolo[3.2.1]oct-3-yl)-amide;
(6-Chloro-5-fluoro-1H-benzoimidazol-2-Yl)-(4-methyl-piperazin-1-yl) -methanone;
(6-Chloro-5-fluoro-1 H-benzoimidazol-2-yl)-piperazin-1-yl-methanone;
(6-Chloro-5-fluoro-1H-benzoimidazol-2-yl)-(4methyl-[1,4]-diazepan-1yl)-methanone;
6-Chloro-5-fluoro-1H-benzoimidazole-2 -carboxylic acid (8-methyl-8-aza-bicyclo[3.2.1]oct-3-yl)-amide;
(5-Chloro-6-methyl-1H-benzoimidazol-2yl)-(4-methyl-piperazin-1-yl) -methanone;
(5-Chloro-6-methyl-1H-benzoimidazol-2-yl)-piperazin-1-yl-methanone;
4-Methyl-1H-benzoimidazole-2-yl)-(3-methyl-piperazin-1-yl)-methanone;
(4-Ethyl-piperazin-1 yl)-(4-methyl-1H-benzoimidazol-2-yl)-methanone;
(4-Methyl-1H-benzoimidazol-2-yl)-(4-methyl-piperazin-1-yl)-methanone;
(4-Methyl-1H-benzoimidazol-2-yl)-piperazin-1-yl-methanone;
(4-methyl-1H-benzoimidazol-2-carboxylic acid(8-methyl-8-aza -bicyclo[3.2.1]oct-3-yl)-amide;
5-Methyl-1H-benzoimidazole-2-carboxylic acid(8-methyl-8-aza bicyclo[3.2.1]oct-3-yl)amide;
(5-Methyl- 1H-benzoimidazol -2-yl)-(4-methyl-piperazin-1-yl)-methanone;
(4 -Methyl-piperazin-1yl)-(5-trifluoromethyl-1H-benzoimidazol-2-yl) -methanone;
Piperazin-1-yl-(5-trifluoromethyl-1H-benzoimidazol-2-yl)-methanone;
(5-fluoro-1H-benzoimidazol-2-yl)-(4-methyl-piperazin-1-yl)-methanone;
(4-Ethyl-piperazin-1-yl)-(5-fluoro-1H-benzoimidazol-2-yl-methanone;
(5-Fluoro-1H-benzoimidazol-2-yl)-piperazin-1-yl)-methanone;
(5-Fluoro-1H-bonzoimidazol 2-yl)-(3 -methyl piperazin-1-yl)-methanone; 5-Fluoro-1H-benzoimidazole-2-carboxylic acid (8-methyl-8-aza-bicyclo[3.2.1]oct-3-yl)-amide; (5-Benzoyl-1H-benzoimidazol-2-yl)-(4-methyl-piperazin-1-yl) -methanone;
(4-Methyl-piperazin-1-yl)-(4-nitro-1H-benzoimidazol-2-yl)-methanone;
(4-1H-benzoimidazol-2yl)-(4-methyl-piperazin-1-yl)-methanone;
(4-Isopropylamino-1H-benzoimidazol-2-yl)-(4-methyl-piperazin-1-yl) methanone.

17. The compound of claim 1 selected from the group consisting of:
(4,6-Difluoro-1H-benzomidazol-2-yl)-(4-methyl-piperazin-1-yl) -methanone;
(4-Methyl-piperazin-1-yl)-(5-nitro-1H-benzoimidazol-2-yl)-methanone;
(5-Fluoro-4-methyl-1H-benzoimidazol-2-yl)-(4-methyl-piperazin-1-yl) -methanone; and
(5-Bromo- 1 H-benzoimidazol-2-yl)-(4-methyl-piperazin-1 -yl) -methanone.

18. The compound of claim 1 selected from the group consisting of: (5,6-Dichloro-1H-benzoimidazol-2-yl)-(4-methyl-piperazin-1-yl) -methanone;
(4,5-Dimethyl-1H-benzoimidazol-2-yl)-(4-methyl-piperazin-1-yl) -methanone;
(5,6-Dimethyl-1H-benzoimidazol-2-yl)-(4-methyl-piperazin-1-yl) -methanone;
(5-Methoxy-1H-benzoimidazol-2.yl)-(4-methyl-piperazin 1-yl) -methanone.

19. A pharmaceutical composition containing a compound of formula (I):

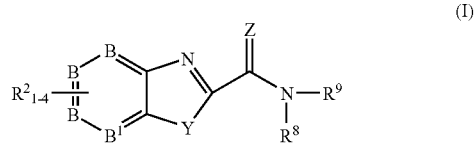

wherein
B and $B^1$ are C;
Y is $NR^z$, where $R^z$ is H or $C_{1-4}$alkyl;
Z is O or S;
$R^8$ is H and $R^9$ is

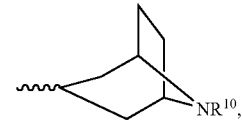

where $R^{10}$ is H or $C_{1-4}$alkyl, or $R^8$ and $R^9$ are taken together with their N of attachment to form

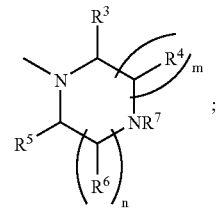

n is 1 or 2;
m is 1 or 2;
n +m is 2 or 3;
$R^2$ are, independently, F, Br, I, $C_{1-4}$alkyl, $C_{1-4}$alkoxy, —$C_{3-6}$cycloalkyl, —$OC_{3-6}$cycloalkyl, —$OCH_2Ph$, —$CF_3$, —$OCF_3$, —$SCF_3$, —OH, —(C=O)$R^K$ (wherein $R^k$ is H, $C_{1-4}$alkyl, —OH, phenyl, benzyl, phenethyl or $C_{1-6}$alkoxy),—(N—$R^r$)(C=O)$R^k$ (where $R^t$ is H or $C_{1-4}$alkyl), —(N—$R^t$)SO$_2$C$_{1-4}$alkyl, —(S═(O)$_p$)—C$_{1-4}$alkyl (wherein p is 0, 1 or 2), nitro, —NR$^l$R$^m$ (wherein R$^l$ and R$^m$ are independently selected from H, C$_{1-4}$alkyl, phenyl, benzyl or phenethyl, or R$^l$ and R$^m$ taken together with the nitrogen to which they are attached, form a 4-7 membered heterocyclic ring with 0 or 1 additional heteroatoms selected from O, S, NH or NC$_{1-4}$alkyl), —SO$_2$NR$^l$R$^m$, —(C═O)NR$^l$R$^m$, cyano or phenyl, where any phenyl or alkyl or cycloalkyl moiety of the foregoing is optionally and independently substituted with between 1 and 3 substituents selected from C$_{1-3}$alkyl, halo, hydroxy, amino, and C$_{1-3}$alkoxy;

$R^3$ and $R^4$ are, independently, H, C$_{1-4}$alkyl, C$_{3-6}$cycloalkyl, C$_{1-4}$alkyl(C$_{3-6}$cycloalkyl), cyano, —CF$_3$, —(CO)NR$^p$R$^q$, —(CO)OR$^r$, CH$_2$NR$^p$R$^q$ or —CH$_2$OR$^r$; where R$^p$, R$^q$ and R$^r$ are independently selected from H, C$_{1-4}$alkyl, C$_{3-6}$cycloalkyl, phenyl, -C$_{1-2}$alkyl(C$_{3-6}$cycloalkyl), benzyl or phenethyl, or R$^p$ and R$^q$ taken together with the nitrogen to which they are attached, form a 4-7 membered heterocyclic ring with 0 or 1 additional heteroatoms selected from O, S, NH or NC$_{1-6}$alkyl, and where any phenyl or alkyl or cycloalkyl moiety of the foregoing is optionally and independently substituted with between 1 and 3 substituents selected from C$_{1-3}$alkyl, halo, hydroxy, amino, and C$_{1-3}$alkoxy;

$R^5$ and $R^6$ are, independently, H or C$_{1-6}$alkyl;

$R^7$ is —R$^a$, —R$^b$R$^a$, —R$^e$—O—R$^a$ or —R$^e$—N(R$^c$)(R$^d$), where R$^a$ is H, cyano, —(C═O)N(R$^c$)(R$^d$), —C(═NH)(NH$_2$), C$_{1-10}$alkyl, C$_{2-8}$alkenyl, C$_{3-8}$cycloalkyl, C$_{4-7}$heterocyclic radical or phenyl, where the C$_{4-7}$heterocyclic radical is attached at a carbon atom and contains one of O, S, NH or NC$_{1-4}$alkyl, and optionally an additional NH or NC$_{2-6}$alkyl in rings of 5 or 6 or 7 members, where R$^b$ is C$_{1-8}$alkylene or C$_{2-8}$alkenylene, where R$^e$ is C$_{2-8}$alkylene or C$_{2-8}$alkenylene, where R$^c$ and R$^d$ are each independently H, C$_{1-4}$alkyl, C$_{2-4}$alkenyl, C$_{3-6}$cycloalkyl or phenyl, or R$^c$ and R$^d$ taken together with the nitrogen to which they are attached, form a 4-7 membered heterocyclic ring with 0 or 1 additional heteroatoms selected from O, S, NH or NC$_{1-6}$ alkyl, and where any phenyl or alkyl or cycloalkyl moiety of the foregoing is optionally and independently substituted with between 1 and 3 substituents selected from C$_{1-3}$alkyl, halo, hydroxy, amino, and C$_{1-3}$alkoxy;

alternatively, $R^7$ may be taken together with an adjacent $R^4$ as well as their carbon and nitrogen of attachment to form a 5, 6 or 7 membered heterocyclic ring, with 0 or 1 additional heteroatoms selected from O, S, NH or NC$_{1-6}$ alkyl, and optionally and independently substituted with between 1 and 3 substituents selected from C$_{1-3}$alkyl, halo, hydroxy, amino, and C$_{1-3}$alkoxy;

and enantiomers, diastereomers and pharmaceutically acceptable salts and esters thereof, with the following provisos, that $R^6$ adjacent to N must be H where $R^4$ adjacent to N is other than H, and that $R^2$ cannot be benzoyl when one of $R^4$ and $R^6$ is methyl and the other is hydrogen.

* * * * *